(12) United States Patent
Tang et al.

(10) Patent No.: US 12,201,700 B2
(45) Date of Patent: Jan. 21, 2025

(54) MICRO- AND NANO-DEVICE FOR CARTILAGE INJURY DETECTION AND TREATMENT

(71) Applicants: Board of Regents, The University of Texas System, Austin, TX (US); Joseph Borrelli, Dallas, TX (US)

(72) Inventors: Liping Tang, Arlington, TX (US); Jun Zhou, Arlington, TX (US); Joseph Borrelli, Dallas, TX (US)

(73) Assignees: Joseph Borreli, Dallas, TX (US); Board of Regents, The University of Texas System, Austin, TX (US)

( * ) Notice: Subject to any disclaimer, the term of this patent is extended or adjusted under 35 U.S.C. 154(b) by 978 days.

(21) Appl. No.: 15/766,039

(22) PCT Filed: Oct. 5, 2016

(86) PCT No.: PCT/US2016/055552
§ 371 (c)(1),
(2) Date: Apr. 5, 2018

(87) PCT Pub. No.: WO2017/062493
PCT Pub. Date: Apr. 13, 2017

(65) Prior Publication Data
US 2018/0296706 A1    Oct. 18, 2018

Related U.S. Application Data

(60) Provisional application No. 62/237,217, filed on Oct. 5, 2015.

(51) Int. Cl.
*A61K 9/00* (2006.01)
*A61K 38/18* (2006.01)
(Continued)

(52) U.S. Cl.
CPC ........ *A61K 49/0054* (2013.01); *A61K 9/0019* (2013.01); *A61K 38/1841* (2013.01);
(Continued)

(58) Field of Classification Search
CPC .................................................. A61K 49/0054
See application file for complete search history.

(56) References Cited

U.S. PATENT DOCUMENTS

| 9,017,644 B2 | 4/2015 | Baker, Jr. et al. |
| 2008/0031850 A1 | 2/2008 | Bader |

(Continued)

FOREIGN PATENT DOCUMENTS

| CN | 103690971 A | 2/2014 |
| JP | 2001231401 | 8/2001 |

(Continued)

OTHER PUBLICATIONS

United States Patent and Trademark Office, International Search Report and Written Opinion for PCT/US2016/055552 dated Jan. 9, 2017, 14 pp.

(Continued)

*Primary Examiner* — Paul W Dickinson
(74) *Attorney, Agent, or Firm* — Edwin S. Flores; Daniel J. Chalker; Chalker Flores, LLP

(57) ABSTRACT

The present invention provides targeting probe, imaging probes, and probes for use as a medicament to treat damaged cartilage, where the probe targets injured tissue and can then be imaged and/or release agents to trigger the migration of surrounding chondrocytes from healthy tissue to injured tissue and/or recruit synovial stem cells.

20 Claims, 11 Drawing Sheets

(51) Int. Cl.
| | |
|---|---|
| A61K 38/19 | (2006.01) |
| A61K 47/55 | (2017.01) |
| A61K 47/61 | (2017.01) |
| A61K 47/69 | (2017.01) |
| A61K 49/00 | (2006.01) |
| C08B 37/08 | (2006.01) |
| G01N 33/68 | (2006.01) |
| G01N 33/82 | (2006.01) |

(52) U.S. Cl.
CPC .......... *A61K 38/195* (2013.01); *A61K 47/551* (2017.08); *A61K 47/61* (2017.08); *A61K 47/6939* (2017.08); *A61K 49/0032* (2013.01); *A61K 49/0052* (2013.01); *A61K 49/0091* (2013.01); *A61K 49/0093* (2013.01); *C08B 37/0072* (2013.01); *G01N 33/6872* (2013.01); *G01N 33/82* (2013.01); *G01N 2333/70585* (2013.01); *G01N 2800/105* (2013.01)

(56) References Cited

U.S. PATENT DOCUMENTS

| | | |
|---|---|---|
| 2011/0256628 A1 | 10/2011 | Galperin et al. |
| 2012/0128741 A1 | 5/2012 | Gravett et al. |

FOREIGN PATENT DOCUMENTS

| | | | |
|---|---|---|---|
| JP | 2007517001 | 6/2007 | |
| JP | 2009544690 | 12/2009 | |
| JP | 2011506734 | 3/2011 | |
| WO | 2007098770 | 9/2007 | |
| WO | 2009077620 A1 | 6/2009 | |
| WO | WO-2009077399 A1 * | 6/2009 | .............. A61P 17/16 |
| WO | 2012145439 | 10/2012 | |
| WO | 2013027854 A1 | 3/2015 | |
| WO | 2017062493 | 4/2017 | |
| WO | 2017062493 A1 | 4/2017 | |

OTHER PUBLICATIONS

Ibrahim, et al., "The Impact of HA Oligomer Content on Physical, Mechanical, and Biologic Properties of Divinyl Sulfone-Crosslinked HA Hydrogels," J. Biomed. Mater. Res. A., vol. 94(2), Aug. 2010, pp. 355-370.
Shimojo, et al., "The Performance of Crosslinking with Divinyl Sulfone as Controlled by the Interplay Between the Chemical Modification and Conformation of Hyaluronic Acid," J. Braz. Chem. Soc., vol. 26, No. 3, 2015, pp. 506-512.
Baker, David W., et al., "Development of optical probes for in vivo imaging of polarized macrophages during foreign body reactions," Acta Biomaterialia, vol. 10, Apr. 13, 2014, pp. 2945-2955.
Chen, Wei-Tsung, et al., "Arthritis imaging using a near-infrared fluorescence folate-targeted probe," Arthritis Res. & Ther., vol. 7 No. 2 Jan. 14, 2005, pp. R310-R317.
Fani, M., et al., "In Vivo Imaging of Folate Receptor Positive Tumor Xenografts Using Novel Ga-NODAGA-Folate Conjugates," Molecurlar Pharmaceutics, vol. 9, Apr. 12, 2012, pp. 1136-1145.
Huang, Peng, et al., "Folic acid-conjugated Silica-modified gold nanorods for X-ray/CT imaging-guided dual-mode radiation and photo-thermal therapy," Biomaterials, vol. 32, Sep. 13, 2011, pp. 9796-9809.
Li, J., et al., "Polyethyleneimine-mediated synthesis of folic acid-targeted iron oxide nanoparticles for in vivo tumor MR maging," Biomaterials, 34, Aug. 7, 2013, pp. 8382-8392.
Zhou, Jun, et al., "In vivo evaluation of medical device-associated inflammation using a macrophage-specific positron emission tomography (PET) imaging proble," Bioorganic & Medicinal Chemistry Letters, vol. 23, Feb. 13, 2013, pp. 2044-2047.
Zhou, Jun, et al., "Real time monitoring of biomaterial-mediated inflammatory responses via macrophage-targeting NIR nanoprobes," Biomaterials, vol. 32, Sep. 3, 2011, pp. 9383-9390.
Zhou, Min, et al., "A Chelator-Free Multifunction [64Cu]CuS Nanoparticle Platform for simultaneous Micro-PET/CT Imaging and Photothermal Ablation Therapy," JACS vol. 132, Oct. 13, 2010, pp. 15351-15358.
Zhou, Min, et al., "Theranostic CuS nanoparticles targeting folate receptors for PET image-guided photothermal therapy," J. Mater. Chem. B., vol. 3, Oct. 19, 2015, pp. 8939-8948.
Borzachhiello, A., et al., "Hyaluronic Acid Based Hydrogels for Regenerative Medicine Applications," BioMed Research International, Mar. 6, 2015, 12 pp.
Fakhari, A., et al., "Applications and Emerging Trends of Hyaluronic Acid in Tissue Engineering, as a Dermal Filler, and in Osteoarthritis Treatment," Acta Biomater, Jul. 2013, vol. 9(7), pp. 7081-7092.
Fakhari, A., Dissertation entitled "Biomedical Application of Hyaluronic Acid Nanoparticles," submitted to Bioengineering of University of Kansas and Defended Jan. 19, 2012, 154 pp.
Ibrahim, S., et al., "The Impact of HA Oligomer Content on Physical, Mechanical, and Biologic Properties of Divinyl Sulfone-Crosslinked HA Hydrogels," J. Biomed. Mater. Res. A., vol. 94(2), Aug. 2010, pp. 355-370.
International Search Report and Written Opinion of the United States Patent and Trademark Office for PCT/US2016/055552 dated Jan. 9, 2017, 14 pp.
Lai, Jui-Yang, "Relationship between structure and cytocompatibility of divinyl sulfone cross-linked hyaluronic acide," Carbohydrate Polymers, Sep. 25, 2013, vol. 101, pp. 203-212.
Shimojo, A.A.M., et al., "The Performance of Crosslinking with Divinyl Sulfone as Controlled by the Interplay Between the Chemical Modification and Conformation of Hyaluronic Acid," J. Braz. Chem. Soc., vol. 26, No. 3, 2015, pp. 506-512.
Xu, X., et al., "Heparin-decorated, hyaluronic acid-based hydrogel particles for the controlled release of bone morphogenetic protein 2," Acta Biomaterialia, Apr. 24, 2011, vol. 7, pp. 3050-3059.
Yeom, et al., "Effect of Cross-Linking Reagents for Hyaluronic Acid Hydrogel Dermal Fillers on Tissue Augmentation and Regeneration," Bioconjugate Chem., Jan. 15, 2010, vol. 21, pp. 240-247.
Yoon, H. Y., et al., "Tumor-targeting hyaluronic acid nanoparticles for photodynamic imaging and therapy," Biomaterials, vol. 33, Feb. 24, 2012, pp. 3980-3989.
Yu, Y., et al., "One-Step 'Click' Method for Generating Vinyl Sulfone Groups on Hydroxyl-Containing Water-Soluble Polymers," BioMacromolecules, Jan. 9, 2012, vol. 13, pp. 937-942.
Extended European Search Report of EP16854239.7 issued by the EPO on Sep. 14, 2018.
Kato, Y., et al., "Accessibility of high molecular weight hyaluronan to articular cartilage and synovium," Clinical Rheumatol. Vol. 21, Oct. 20, 2008, pp. 20-31.
Rey-Rico, A., et al., "Adapted chondrogenic differentiation of human mesenchymal stem cells via controlled release of TGF-B1 from poly(ethylene oxide)-terephtalate/poly(butylene tereptalate) multiblock scaffolds," Society for Biomaterials, Apr. 9, 2014, 14 pp.
Turk, M.J., et al., "Folate-Targeted Imaging of Activated Macrophages in Rats with Adjuvant-Induced Arthritis," Arthritis & Rheumatism, vol. 46, No. 7, Jul. 2002, pp. 1947-1955.
Shcharbin, et al. "How to study dendrimers and dendriplexes III. Biodistribution, pharmacokinetics and toxicity in vivo" Journal of Controlled Release, Available online Mar. 4, 2014, 181 (2014) 40-52.
Muller, et al. "Determination of Molecular Weight, Particle Size, and Density of High Number Generation PAMAM Dendrimers Using MALDI-TOF-MS and nES-GEMMA" Macromolecules 2007, 40, 5599-5605, Published on Web Jun. 20, 2007.
Pradal, et al. "Effect of particle size on the biodistribution of nano- and microparticles following intra-articular injection in mice" International Journal of Pharmaceutics 498 (2016) 119-129, Available online Dec. 10, 2015.
Naor, D., et al., "Review CD44 in rheumatoid arthritis," Arthritis Res Ther, Feb. 28, 2003, 5:105-115.

(56) References Cited

OTHER PUBLICATIONS

China National Intellectual Property Administration, Examination Report for China Patent Appl. No. 201680069894.7 dated Oct. 10, 2021, 23 pp.
China National Intellectual Property Administration, 2nd Examination Report for China Patent Appl. No. 201680069894.7 dated Jul. 5, 2021, 23 pp.
European Patent Office, Communication pursuant to Article 94(3) EPC for EP16854239.7 dated Jun. 3, 2019, 4 pp.
European Patent Office, Communication pursuant to Article 94(3) EPC for EP16854239.7 dated Aug. 12, 2019, 5 pp.
European Patent Office, Communication pursuant to Article 94(3) EPC for EP16854239.7 dated Nov. 18, 2019, 6 pp.
European Patent Office, Communication pursuant to Article 94(3) EPC for EP16854239.7 dated Apr. 23, 2020, 4 pp.
European Patent Office, Communication pursuant to Article 94(3) EPC for EP16854239.7 dated Jul. 14, 2020, 4 pp.
European Patent Office, Communication pursuant to Article 94(3) EPC for EP16854239.7 dated Sep. 4, 2020, 5 pp.
European Patent Office, Communication pursuant to Article 94(3) EPC for EP16854239.7 dated Feb. 17, 2020, 7 pp.
Japan Patent Office, Notification of Refusal for Japan Appl. No. 2018-536714, Dated May 27, 2019, 13 pp.
Japan Patent Office, Notification of Refusal for Japan Appl. No. 2018-536714, Dated Dec. 9, 2019, 13 pp.

\* cited by examiner

FIGURE 3A
FIGURE 3B
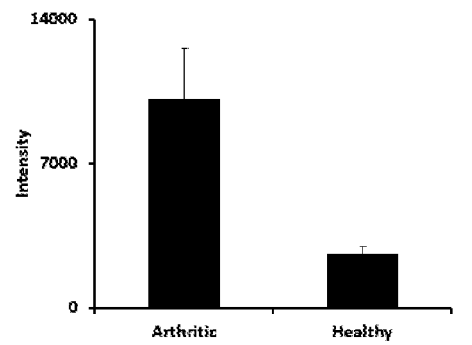
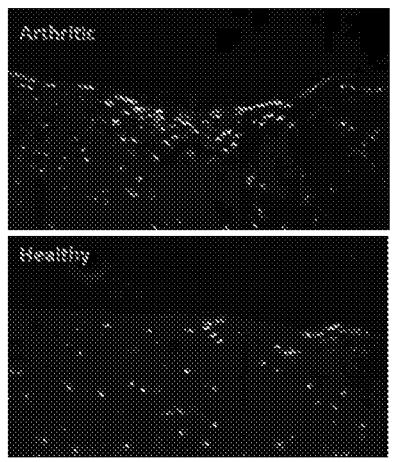
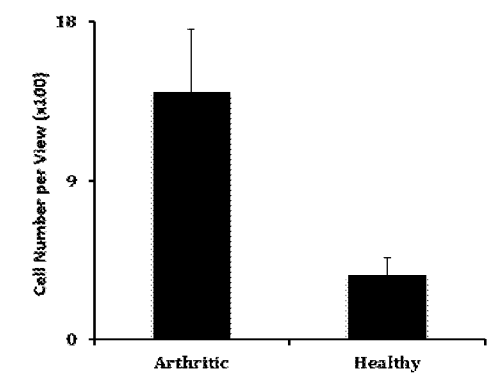
FIGURE 3C
FIGURE 3D
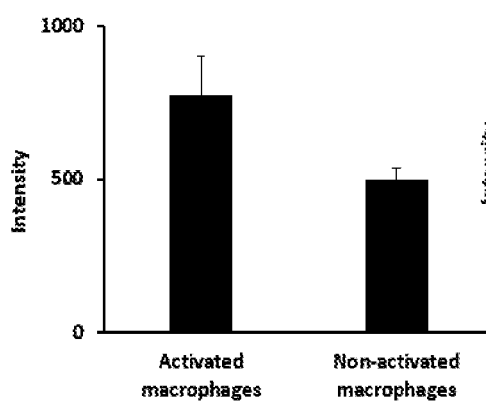
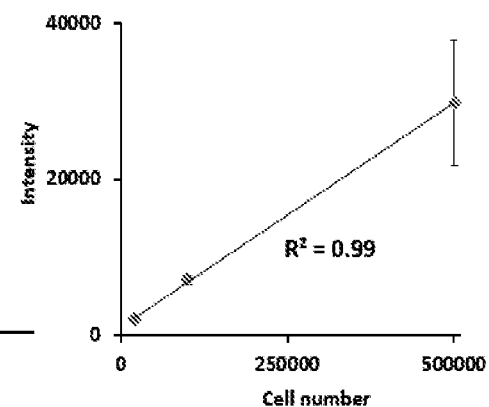
FIGURE 4A
FIGURE 4B Xiphoid injury animal
Control
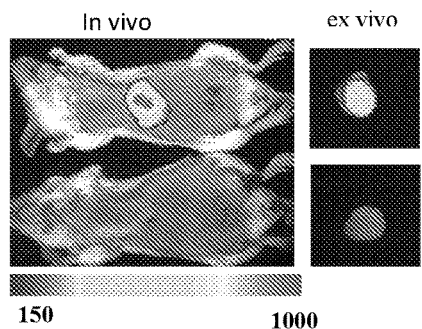
150    1000
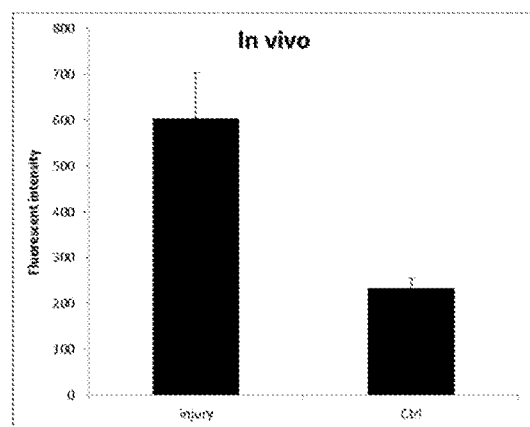
FIGURE 12A    FIGURE 12B    FIGURE 12C
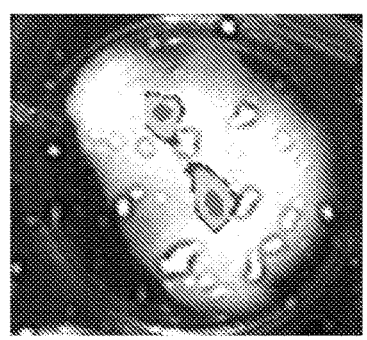
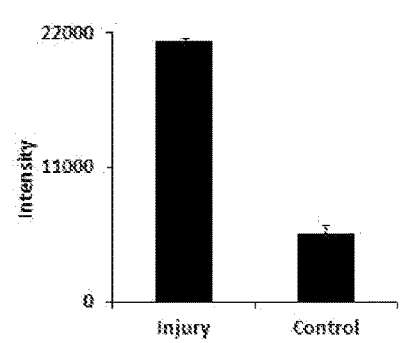
FIGURE 13A    FIGURE 13B

MICRO- AND NANO-DEVICE FOR CARTILAGE INJURY DETECTION AND TREATMENT

CROSS-REFERENCE TO RELATED APPLICATIONS

This application is the National Stage of International Application No. PCT/US2016/055552, filed on Oct. 5, 2016 claiming the priority of U.S. Provisional Patent Application Ser. No. 62/237,217 filed on Oct. 5, 2015, the contents of each of which are incorporated by reference herein.

STATEMENT OF FEDERALLY FUNDED RESEARCH

This invention is based in part upon work supported by the Department of Defense Congressionally Directed Medical Research Programs (DOD CDMRP) under contract No. W81XWH-14-0459. The U.S. Government has certain rights to this invention.

TECHNICAL FIELD OF THE INVENTION

This invention is on the development of microscaffolds for the detection and treatment of injured cartilages. Our invention is based on the design of micro- or nano-sized scaffolds which can (1) diagnose the injured cartilages by targeting activated/injured cells and (2) repair the injured cartilages by releasing biomolecules to promote the autologous stem cell and chrondrocytes responses (recruitment and cartilage regenerations).

BACKGROUND ART

Without limiting the scope of the invention, its background is described in connection with compositions and methods for the development of microscaffolds for the detection and treatment of injured cartilages.

Scaffolds are made of biodegradable materials which can be administered via needle injection and also have the ability to release biomolecules. For cell targeting, scaffolds contain ligands unique to activated/injured/or apoptotic cells. These ligands include hyaluronic acid for CD44 receptor (upregulated on activated chondrocytes), folic acid for activated macrophages. The ligands can be part of the scaffolds or be coated on and inside the scaffolds.

Biomolecules for promoting stem cell responses include erythropoietin, stromal derived factors. The biomolecules can be loaded into the scaffold carrier via physical adsorption or chemical conjugations.

DISCLOSURE OF THE INVENTION

Post-traumatic osteoarthritis (PTOA) is one of the most common forms of arthritis. PTOA is believed to be the result of articular cartilage injury. X-rays and MRI have traditionally been used to examine the anatomical changes that occur in the damaged cartilage. Unfortunately, there are no methods to detect early cartilage injury particularly at the cellular level. Previous studies have shown that there is a good relationship between chondrocyte apoptosis and proteoglycan depletion in PTOA.

Arthritis is a joint disorder featuring inflammation. There are many types of arthritis. The types of arthritis range from those related to wear and tear of cartilage to those associated with inflammation resulting from overactive immune responses.

Standard treatments for arthritis start with weight loss, low impact exercises and muscle strengthening surrounding the joint, and oral non-steroidal anti-inflammatory drugs (NSAIDs). To reduce the systemic complications often associated with chronic use of NSAIDs and steroids, cortisone or lubricious polymer (Hylamers) are injected intra-articularly. Despite their effectiveness in reducing discomfort and many of the symptoms, these pharmacological treatments are ineffective in altering the natural history of arthritis. The failure of these treatments necessitates surgery which typically involves debridement, reconstruction and replacement of worn-out joint surfaces with artificial implants. Like pharmacological approaches, conventional surgical therapies fail to restore full function of the articular cartilage joints. In addition, joint prosthetics may integrate poorly with the native tissue, elicit foreign body response and have a limited life-span, requiring multiple surgical interventions every ten to fifteen years. The lack of effective and permanent therapies necessitates a new therapeutic approach which can improve articular healing while reducing inflammatory responses. This invention is designed as a permanent cure for arthritis.

The present invention provides targeting probe for imaging damaged cartilage. The targeting probe can target injured tissue and then release chemokines to trigger the migration of surrounding chondrocytes from healthy tissue to injured tissue. The targeting probe can target injured tissue and then release chemokines to recruit synovial stem cells. The stem cells are then differentiated into chondrocytes which then participate in the cartilage regeneration. In some embodiments, the claimed invention may perform all three of those functions, whereas in other embodiments the claimed invention may perform all one or two of those functions.

The present invention provides an arthritic cartilage targeting probe for use as a medicament to target and/or treat arthritic cartilage, wherein the arthritic cartilage targeting probe comprises a biocompatible hyaluronic acid polymer crosslinked by a vinyl sulfone to form a crosslinked biopolymer, wherein the biocompatible hyaluronic acid polymer has a molecular weight of 10K to 1.5M and the crosslinking ratio of the biocompatible HA polymer:vinyl sulfone is between 4:1 and 1:4 and the crosslinked biopolymer has a diameter of greater than about 200 nm to modulate internalization; a ligand in contact with the crosslinked biopolymer, wherein the ligand is hyaluronic acid that interacts with a CD44 receptor, folic acid that interacts with a folate receptor or both; and a detectable tag in contact with the crosslinking agent, first biocompatible polymer, the ligand or a combination thereof.

The present invention provides a damaged cartilage targeting probe for use as a medicament to target and/or treat damaged cartilage, wherein the damaged cartilage targeting probe comprises: a biocompatible hyaluronic acid polymer crosslinked by a vinyl sulfone to form a crosslinked biopolymer, wherein the biocompatible hyaluronic acid polymer has a molecular weight of 10K to 1.5M and the crosslinking ratio of the biocompatible HA polymer:vinyl sulfone is between 4:1 and 1:4 and the crosslinked biopolymer has a diameter of greater than about 200 nm to modulate internalization; a ligand in contact with the crosslinked biopolymer, wherein the ligand interacts with one or more cell surface targets; and a detectable tag in contact with the crosslinking agent, first biocompatible polymer, the ligand or a combination thereof.

The present invention provides The use of a damaged cartilage targeting probe for identifying damaged cartilage comprising: providing a damaged cartilage targeting probe comprises a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4; wherein the crosslinked biopolymer has a diameter of greater than about 200 nm to modulate internalization; a ligand in contact with the crosslinked biopolymer, wherein the ligand interacts with one or more cell surface targets; and a detectable tag in contact with the crosslinking agent, first biocompatible polymer, the ligand or a combination thereof; contacting a cartilage suspected of being damaged with the damaged cartilage targeting probe; and detecting the damaged cartilage targeting probe.

The present invention provides a cartilage targeting probe for use as a medicament to treat damaged cartilage by recruiting stem cells, chondrocytes or both to the damaged cartilage, wherein the cartilage targeting probe comprises: a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4 and the crosslinked biopolymer has a diameter of greater than about 200 nm to modulate internalization; a ligand in contact with the crosslinked biopolymer, wherein the ligand interacts with one or more cell surface targets; one or more chemokines selected from SDF 1, SDF 1β, Epo, CCL2, CCL16, VEGF, TGF-β1 and TGF-β3, associated with the polymer targeting probe, wherein the one or more chemokines are released to recruit stem cells, chondrocytes or both; and a detectable tag in contact with the crosslinking agent, first biocompatible polymer, the ligand or a combination thereof.

The present invention provides a cartilage targeting probe for use as a medicament to treat damaged cartilage by increasing chondrogenic differentiation, wherein the cartilage targeting probe comprises: a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4 and the crosslinked biopolymer has a diameter of greater than about 200 nm to modulate internalization; a ligand in contact with the crosslinked biopolymer, wherein the ligand interacts with one or more cell surface targets; one or more TGF active agents selected from TGF-β1 and TGF-β3 associated with the polymer targeting probe, wherein the one or more TGF active agents are released to trigger higher chondrogenic differentiation; and a detectable tag in contact with the crosslinking agent, first biocompatible polymer, the ligand or a combination thereof.

The present invention provides the use of a damaged cartilage targeting probe for identifying damaged cartilage having small injuries down to 1 mm comprising: providing a damaged cartilage targeting probe comprises a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4; wherein the crosslinked biopolymer has a diameter of greater than about 200 nm to modulate internalization; a ligand in contact with the crosslinked biopolymer, wherein the ligand interacts with one or more cell surface targets; and a detectable tag in contact with the crosslinking agent, first biocompatible polymer, the ligand or a combination thereof; contacting a cartilage suspected of having small injuries down to 1 mm with the damaged cartilage targeting probe; and detecting the damaged cartilage targeting probe.

In some embodiments the ligand is hyaluronic acid and the one or more cell surface targets is a CD44 receptor. In other embodiments the ligand is a folic acid and the one or more cell surface targets is a folate receptor.

The present invention provides a damaged/injured cartilage imaging probe for use as a medicament to target and/or treat damaged cartilage, wherein the damaged cartilage imaging probe comprises a biocompatible hyaluronic acid polymer crosslinked by a vinyl sulfone to form a crosslinked biopolymer, wherein the biocompatible hyaluronic acid polymer has a molecular weight of 10K to 1.5M and the crosslinking ratio of the biocompatible HA polymer:vinyl sulfone is between 4:1 and 1:4 and the crosslinked biopolymer has a diameter of greater than about 200 nm to modulate internalization; a ligand in contact with the crosslinked biopolymer, wherein the ligand is hyaluronic acid that interacts with a CD44 receptor, folic acid that interacts with a folate receptor or both; and a detectable tag in contact with the crosslinking agent, first biocompatible polymer, the ligand or a combination thereof, wherein the detectable tag can be detected at the damaged cartilage and used to generate an image of the damaged cartilage.

The damage to the cartilage can be from any source including mechanical trauma, physical trauma compression trauma, arthritic damage, inflammatory damage or a combination thereof.

In any of the embodiments the polymer targeting probe can comprise biocompatible hyaluronic acid polymer having a molecular weight of about 10K, 60K, 700k, 1.5M or incremental variations thereof (e.g., 8K, 9K, 10K, 11K, 12K, 13K, 14K, 15K, 16K, 17K, 18K, 19K, 20K, 21K, 22K, 23K, 24K, 25K, 26K, 27K, 28K, 29K, 30K, 31K, 32K, 33K, 34K, 35K, 36K, 37K, 38K, 39K, 40K, 41K, 42K, 43K, 44K, 45K, 46K, 47K, 48K, 49K, 50K, 51K, 52K, 53K, 54K, 55K, 56K, 57K, 58K, 59K, 60K, 61K, 62K, 63K, 64K, 65K, 66K, 67K, 68K, 69K, 70K, 71K, 72K, 73K, 74K, 75K, 76K, 77K, 78K, 79K, 80K, 81K, 82K, 83K, 84K, 85K, 86K, 87K, 88K, 89K, 90K, 100K, 110K, 120K, 130K, 140K, 150K, 160K, 170K, 180K, 190K, 200K, 210K, 220K, 230K, 240K, 250K, 260K, 270K, 280K, 290K, 300K, 310K, 320K, 330K, 340K, 350K, 360K, 370K, 380K, 390K, 400K, 410K, 420K, 430K, 440K, 450K, 460K, 470K, 480K, 490K, 500K, 510K, 520K, 530K, 540K, 550K, 560K, 570K, 580K, 590K, 600K, 610K, 620K, 630K, 640K, 650K, 660K, 670K, 680K, 690K, 700K, 710K, 720K, 730K, 740K, 750K, 760K, 770K, 780K, 790K, 800K, 810K, 820K, 830K, 840K, 850K, 860K, 870K, 880K, 890K, 900K, 1M; 1.2M; 1.3M; 1.4M; 1.5M; 1.6M; 1.7M; 1.8M; 1.9M; 1.10M; 1.11M; 1.12M; 1.13M; 1.14M; 1.15M; 1.16M; 1.17M; 1.18M; 1.19M; 1.20M; 1.21M; 1.22M; 1.23M; 1.24M; 1.25M; 1.26M; 1.27M; 1.28M; 1.29M; 1.30M; 1.31M; 1.32M; 1.33M; 1.34M; 1.35M; 1.36M; 1.37M; 1.38M; 1.39M; 1.40M; 1.41M; 1.42M; 1.43M; 1.44M; 1.45M; 1.46M; 1.47M; 1.48M; 1.49M; 1.50M; 1.51M; 1.52M; 1.53M; 1.54M; 1.55M; 1.56M; 1.57M; 1.58M; 1.59M; 1.60M; 1.61M; 1.62M; 1.63M; 1.64M;

1.65M; 1.66M; 1.67M; 1.68M; 1.69M; or 1.70M) and it has a crosslinking ratio is 1:4, 1:3, 1:2, 1:1, 1:3.9, 1:3.5, 1:2.3, 4:1, 3:1, 2:1 and incremental variations thereof (e.g., 1:4; 1.1:4; 1.2:4; 1.3:4; 1.4:4; 1.5:4; 1.6:4; 1.7:4; 1.8:4; 1.9:4; 2:4; 2.1:4; 2.2:4; 2.3:4; 2.4:4; 2.5:4; 2.6:4; 2.7:4; 2.8:4; 2.9:4; 3:4; 3.1:4; 3.2:4; 3.3:4; 3.4:4; 3.5:4; 3.6:4; 3.7:4; 3.8:4; 3.9:4; 4:1; 4:1.1; 4:1.2; 4:1.3; 4:1.4; 4:1.5; 4:1.6; 4:1.7; 4:1.8; 4:1.9; 4:2; 4:2.1; 4:2.2; 4:2.3; 4:2.4; 4:2.5; 4:2.6; 4:2.7; 4:2.8; 4:2.9; 4:3.0; 4:3.1; 4:3.2; 4:3.3; 4:3.4; 4:3.5; 4:3.6; 4:3.7; 4:3.8; or 4:3.9)

The detectable tag may be a fluorescent dye, a radioactive tag, a metal, a nanoparticle or a combination thereof. In any of the embodiments the polymer targeting probe may be biodegradable or partially biodegradable.

The polymer targeting probe may include one or more chemokines or one or more TGF active agents bound to the crosslinked biopolymer, releasably associated, disposed in the crosslinked biopolymer, spray coated on the crosslinked biopolymer or a combination thereof.

The crosslinked biopolymer may form one or more pores to carry active agents, e.g., the one or more pores to carry one or more chemokines or one or more TGF active agents for extended release over time. depending on the active agent carried and the release rate or profile desired crosslinking may be varied to form pores having an average diameter of 1, 2, 3, 4, 5, 6, 7, 8, 9, 10, 11, 12, 13, 14, 15, 16, 17, 18, 19, 20, 21, 22, 23, 24, 25, 26, 27, 28, 29 nm or less than 1 nm or greater than 29 nm and incremental variations of 0.1, 0.2, 0.3, 0.4, 0.5, 0.6, 0.7, 0.8, or 0.9 for each (e.g., X.1, X.2, X.3, X.4, X.5, X.6, X.7, X.8, or X.9, wherein X is 1, 2, 3, 4, 5, 6, 7, 8, 9, 10, 11, 12, 13, 14, 15, 16, 17, 18, 19, 20, 21, 22, 23, 24, 25, 26, 27, 28, or 29; specific examples include 3.1, 3.2, 3.3, 3.4, 3.5, 3.6, 3.7, 3.8, 3.9, or 11.1, 11.2, 11.3, 11.4, 11.5, 11.6, 11.7, 11.8, 11.9 or 20.1, 20.2, 20.3, 20.4, 20.5, 20.6, 20.7, 20.8, 20.9).

The polymer targeting probe can be used to contact the one or more targets in less than 15 minutes to allow the quick detection within 15 minutes. The polymer targeting probe can be intra-articular injected.

The present invention provides a composition and method for the directed treatment of damaged cartilage. The present invention can be used as an identification mechanism to locate damaged cartilage using the ligand to direct the cartilage damaged imaging probe to the damaged cartilage and the first detectable tag to identify the location of the cartilage damaged imaging probe in the body. A second cartilage targeting probe can be used as a medicament to treat damaged cartilage by recruiting stem cells, chondrocytes or both to the damaged cartilage. The ligand is used to direct the second cartilage targeting probe to the damaged cartilage where the one or more chemokines are released from the second cartilage targeting probe to recruit stem cells, chondrocytes or both to the damaged cartilage. The second cartilage targeting probe can have a second detectable tag to identify the location of the second cartilage targeting probe. A third cartilage targeting probe can be used as a medicament to treat damaged cartilage by increasing chondrogenic differentiation. The third cartilage targeting probe includes a ligand used to direct the third cartilage targeting probe to the damaged cartilage where the one or more TGF active agents are released from the third cartilage targeting probe to trigger higher chondrogenic differentiation. The third cartilage targeting probe can have a third detectable tag to identify the location of the second cartilage targeting probe. In this example, there are 3 probes with 3 different detectable tags allowing each to be imaged and identified as to location and delivery. However in some instances the detectable tag may be the same for each. Similarly, it is apparent that the number of probes may be reduced by combining the individual probes into 2 or even 1 probe. For example a single imaging probe can be used followed by local injection of a second probe that releases chemokines to recruit stem cells, chondrocytes or both to the damaged cartilage and also releases one or more TGF active agents to trigger higher chondrogenic differentiation. For example the present invention provides an damaged cartilage probe for use as a medicament for targeted treatment of damaged cartilage, wherein the damaged cartilage probe comprises: a cartilage damaged imaging probe for identifying damaged cartilage, wherein the cartilage damaged imaging probe comprises a biocompatible hyaluronic acid polymer crosslinked by a vinyl sulfone to form a crosslinked biopolymer, wherein the biocompatible hyaluronic acid polymer has a molecular weight of 10K to 1.5M and the crosslinking ratio of the biocompatible HA polymer:vinyl sulfone is between 4:1 and 1:4 and the crosslinked biopolymer has a diameter of greater than about 200 nm to modulate internalization; a ligand in contact with the crosslinked biopolymer, wherein the ligand is hyaluronic acid that interacts with a CD44 receptor, folic acid that interacts with a folate receptor or both; and a detectable tag in contact with the crosslinking agent, first biocompatible polymer, the ligand or a combination thereof, wherein the first detectable tag can be detected at the damaged cartilage and used to generate an image of the damaged cartilage; and a cartilage targeting probe for use as a medicament to treat damaged cartilage by recruiting stem cells, chondrocytes or both to the damaged cartilage, wherein the cartilage targeting probe comprises: a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4 and the crosslinked biopolymer has a diameter of greater than about 200 nm to modulate internalization; a ligand in contact with the crosslinked biopolymer, wherein the ligand interacts with one or more cell surface targets; one or more chemokines selected from SDF 1, SDF 1β, Epo, CCL2, CCL16, VEGF, TGF-β1 and TGF-β3, associated with the polymer targeting probe, wherein the one or more chemokines are released to recruit stem cells, chondrocytes or both; and optionally a second detectable tag in contact with the crosslinking agent, first biocompatible polymer, the ligand or a combination thereof; and optionally a chondrogenic differentiation probe for use as a medicament to treat damaged cartilage by increasing chondrogenic differentiation, wherein the chondrogenic differentiation probe comprises: a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4 and the crosslinked biopolymer has a diameter of greater than about 200 nm to modulate internalization; a ligand in contact with the crosslinked biopolymer, wherein the ligand interacts with one or more cell surface targets; one or more TGF active agents selected from TGF-β1 and TGF-β3 associated with the polymer targeting probe, wherein the one or more TGF active agents are released to trigger higher chondrogenic differentiation; and a third detectable tag in contact with the crosslinking agent, first biocompatible polymer, the ligand or a combination thereof.

DESCRIPTION OF THE DRAWINGS

For a more complete understanding of the features and advantages of the present invention, reference is now made to the detailed description of the invention along with the accompanying figures and in which:

FIGS. 2A and 2C are fluorescent images showing of CD44-targeting probe-incubated naïve and activated (LPS-treated) chondrocytes. FIG. 2B shows the fluorescent images intensity of CD44-targeting probe-incubated naïve and activated (LPS-treated) chondrocytes. FIG. 2D shows the number of activated chondrocyte cells.

FIGS. 3A-3D show ex vivo assessment of CD44-targeting probes to diagnose human arthritic cartilage tissues. FIG. 3A is a fluorescent image of arthritic cartilage tissue vs. healthy cartilage tissue with FIG. 3B showing the quantified tissue-associated fluorescent intensities. FIG. 3C are tissue cross-section images taken and then overlapped with cell nucleus images for arthritic cartilage tissue vs. healthy cartilage tissue with FIG. 3D showing the quantified number of the CD44+ cells on both arthritic and healthy cartilage tissues.

FIGS. 4A and 4B show an in vitro assessment of FA receptor-targeting probe to detect inflamed cells. FIG. 4A shows an increased fluorescent intensity of FA receptor-targeting probe on LPS-treated activated macrophages by control with naïve cells. FIG. 4B is a plot showing the linear relationship between cell-associated fluorescent intensity and the number of activated macrophage.

FIG. 11A is an image that shows the FA receptor-targeting probes are preferentially accumulate on mechanically injured tissue (top) than healthy tissue (bottom). FIG. 11B is a graph of the amounts of probe accumulated on both injured and healthy tissue were quantified and then compared (right).

FIGS. 12A-12C show the diagnose of mechanically injured xiphoid using CD44 targeting probes. FIG. 12A shows CD44-targeting probes accumulated on mechanically injured cartilage but not healthy one (top). The amounts of probe accumulated on both injured and healthy tissue were quantified and then compared (bottom). FIG. 12B shows the ex vivo result and FIG. 12C shows quantifies the fluorescence.

FIG. 13A is an image and FIG. 13B is a plot quantification of 1 mm diameter-sized cartilage injury. CD44-targeting HA-based probes were found to preferentially accumulate at the injured site.

DESCRIPTION OF EMBODIMENTS

Figure 1A:
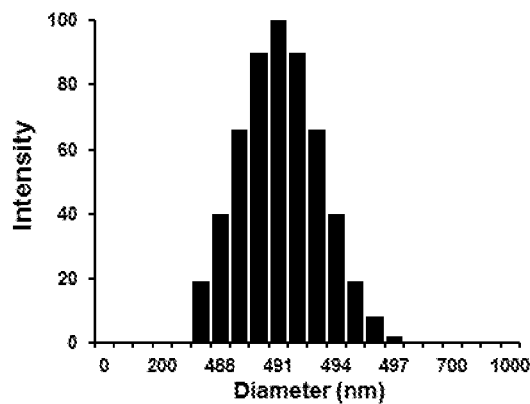
FIG. 1A is a plot of the size distribution of the HA nanoparticle characterization by DLS (left) and FIG. 1B is a SEM image.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Biocompatible and degradable polymers can be used to fabricate the nano- or micro-scaffolds. To demonstrate such capability, hyaluronic acid (HA) was used as a model material for scaffold fabrication.

As used therein the terms "micro-/nano-particles," "nano-particles," "micro-particles," scaffold," "damaged/injured cartilage targeting probe," "polymer targeting probe," "probe" and variations thereof are interchangeable and used to denote the biocompatible hyaluronic acid polymer cross-linked by a vinyl sulfone and may in some embodiments include a ligand, a detectable tag and/or one or more active agents.

Fabrication of HA micro-/nano-particles. HA micro-/nano-particles can be fabricated using a microemulsion system. Briefly, the aqueous phase was prepared by dissolving HA (60 mg, 700K) in a 3 ml of NaOH (0.2 M) solution; the organic phase was prepared by dissolved 0.2 M Aerosol OT and 0.04 M 1-heptanol in isooctane (50 ml). The aqueous solution was added dropwise into the organic phase and then the mixture was immediately homogenized for 10 minutes. Vinyl sulfone (100 µl) was subsequently added to the microemulsion and the mixture was homogenized again to disperse DVS. The reaction was allowed to proceed for 1 hour at ambient temperature with vigorous stirring. HA particles were collected by precipitation in acetone. The precipitated HA particle pellet was re-dispersed into DI water, followed by centrifugation at 1000 rpm for 10 min to remove micro-size HA. Finally, the HA nanoparticles was collected by centrifugation of the supernatant at 5000 rpm. The collected HA nanoparticles were thoroughly washed with water, ethanol and acetone before being dried at 37° C. overnight. To prepare CD44-targeting optical nanoprobe, 50 mg of the as-prepared HA nanoparticles and 1 mg of CF™647 dye (Biotium, CA) was sequentially dispersed into PBS buffer (pH:4.5; 3.0 ml), and then 1-ethyl-3-(3-dimethylaminopropyl) carbodiimide hydrochloride (EDC) (at molar ratio of dye to EDC:1:10) was added into the mixture to initiate dye conjugation into HA nanoparticles. After 24 hours, the reaction solution was dialyzed exhaustedly against DI water and the purified CF™647-labelling HA nanoparticles were collected and dried for future use. Conjugation efficiency of the dye is estimated to be 10 nanomole per milligram of the dried HA particle using UV-vis spectrometer. The size of as-prepared CD44-targeting probe (or HA particles) was characterized by dynamic light scattering (DLS) and scanning electron microscopy (SEM) (App.1), The average diameter of HA particles was around 500 nm. Zeta potential of HA particles is around −41 mv. SEM image shows a reduction of particle size (~300 nm) due to the shrinkage of particles associated with drying during sample preparation for SEM measurement. Physicochemical characteristics of particles such as size and surface properties play crucial roles in the cellular uptake. According to "wrapping time" of the membrane theory, larger-size particles require stronger driving force and additional energy in the cellular internalization process, and those with larger size (>150 nm) would be mostly excluded from non-phagocytic cellular internalization. Previous studies reveal that non-phagocytic cells favored the uptake of smaller particles. On the other hand, negatively-charged particles reduce cell uptake due to the increasing electrostatic repulsion forces between the NPs and the cell membranes. Therefore, the as-prepared HA particle probe has less chance to nonspecifically bind to non-targeting cells/tissues, leading to higher imaging resolutions. Therefore, the HA particle probe used here is suitable for targeting of CD44 receptor on cell membrane.

Figure 1B:
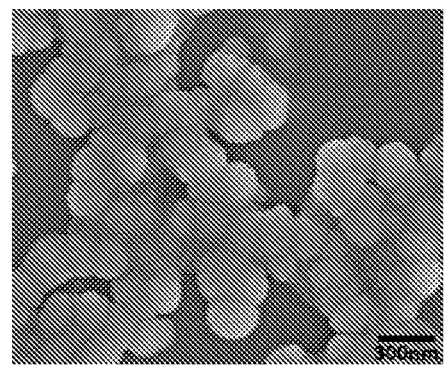

FIG. 1A is a plot of the size distribution of the HA nanoparticle characterization by DLS (left) and FIG. 1B is a SEM image. FIG. 2 shows in vitro CD44-targeting HA particle targeting to normal and activated chondrocytes.

Figure 2A:
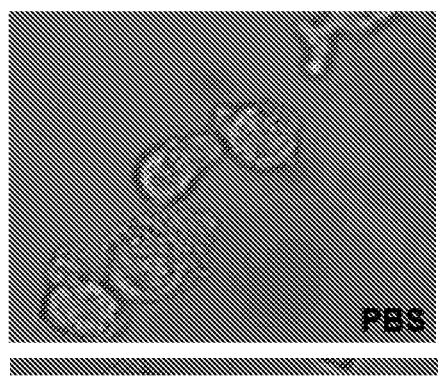
FIGS. 2A-2D show in vitro CD44-targeting HA particle targeting to normal and activated chondrocytes.
Figure 2B:
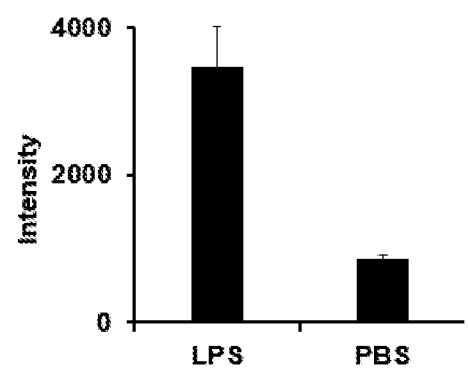
Figure 2C:
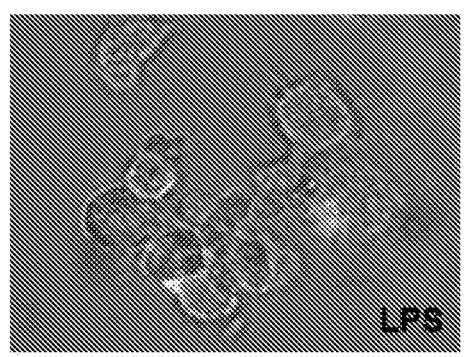
Figure 2D:
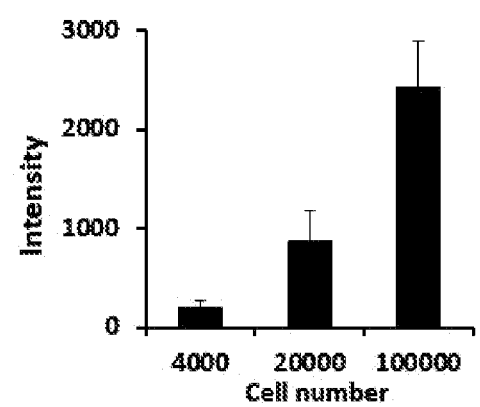

FIGS. 2A and 2C are fluorescent images showing of CD44-targeting probe-incubated naïve and activated (LPS-treated) chondrocytes. FIG. 2B shows the fluorescent images intensity of CD44-targeting probe-incubated naïve and activated (LPS-treated) chondrocytes. FIG. 2D shows that the cell-associated fluorescent intensities increase with the increasing numbers of activated chondrocyte cells. The ability of HA particles to target CD44 receptors on chondrocytes in vitro was investigated using bovine chondrocytes. LPS treatment (50 ng/ml for 24 hours) was used to activate chondrocytes to express CD44 receptor. Naïve and activated chondrocytes ($2\times10^5$/well) were incubated with CF™647 dye-labelling CD44-targeting HA particles (0.1 mg/ml) for one hour @ 37° C. After washed with PBS 2×, HA nanoparticle accumulation on cell surfaces were observed using fluorescent microscope and cell-associated fluorescent intensities were recorded using plate reader. Fluorescent images (FIG. 2A, 2C) showed that LPS-treated chondrocytes are associated with large number of CD44 targeting HA particles. Quantitative analysis further reveals that fluorescent intensity from LPS-treated chondrocytes is ~4 times higher than controls (FIG. 2B). This is because HA particles interacts with CD44 receptors which are highly up-regulated on activated chondrocytes (FIG. 2D). Furthermore, there is a linear relationship between the fluorescent intensities and activated chondrocyte numbers. Our results support that HA particles can be used for targeting CD44-expressed chondrocytes and CD44-targeting probes can be used to assess the numbers of CD44+ arthritic cells.

FIG. 3 shows ex vivo assessment of CD44-targeting probes to diagnose human arthritic cartilage tissues. FIG. 3A is a fluorescent image of arthritic cartilage tissue vs. healthy cartilage tissue with FIG. 3B showing the quantified tissue-associated fluorescent intensities. FIG. 3C are tissue cross-section images taken and then overlapped with cell nucleus images for arthritic cartilage tissue vs. healthy cartilage tissue with FIG. 3D showing the quantified number of the CD44+ cells on both arthritic and healthy cartilage tissues. It is well established that inflamed, injured or arthritic cartilage expressed high level of CD44 receptor. The ability of CD44-targeting probe (HA particles) to target arthritic cartilage was assessed in vitro. Both diseased and healthy tissue were placed in a 6-well plate. CF™647-conjugated CD44-targeting probe were added into each well (1.0 mg/ml) and then incubated at 37° C. for 30 minutes. Discarded human arthritic and inflamed cartilages following total knee or hip replacement were used in this investigation. The ability of CD44-targeting probe to target arthritic and inflamed cartilages was quantified using a Kodak imaging system. Our data has shown that diseased (arthritic) tissue accumulated 4× more CD44-targeting probes than control tissue (healthy cartilage). IHC staining (CD44 staining) reveals the enhanced CD44 expression in the arthritic cartilage tissue. There is approximately 3.8× higher CD44 in arthritic cartilage tissue than in the healthy cartilage tissue. These results support the conclusion that the CD44-targeting probe (HA particles) can be used to detect arthritic cartilage tissue.

Folate receptor targeting probes for diagnosing arthritic cartilage. Many reports have shown that injured, damaged, or diseased cartilage have up-regulated folic acid (FA) receptors. By targeting FA receptor, we have developed novel probes to detect injured, damaged or diseased cartilage. It has been shown that activated macrophages and inflamed cells on cartilage tissue have high level of FA receptor expression on their surfaces. By detecting extent of FA receptor-expression cells, we will be able to diagnose arthritic cartilage. FA receptor has high affinity to folate and its fragment. The probes can be fabricated using a wide variety of the materials, including hyaluronic acid (HA), polyethylene glycol etc. Particles used include, but not limited to, hyaluronic acid micro- or nano-size particles, chitosan particles, gelatin particles, collagen particles, albumin particles, PLGA/PLA particles and polyethylene glycol nanoparticles etc. For the folate receptor targeting property, the probes' surfaces have to possess the whole molecules or fragment of folate/folic acid. For visualization/visual diagnosis, probe should be conjugated with fluorescent dyes such as FITC, Fluor® and CY®.

Imaging probes to detect FA receptor-positive inflamed cells can be prepared with fluorescent dye-labeling particles conjugated with FA and FA derivatives. To prepare FA receptor-targeting probe, FA was first coupled onto the one end of amine-PEG-amine ($M_w$: 5K) via EDC chemistry to obtain. 70 mg of FA-PEG-NH$_2$ and 10 mg of CF™647-labelling HA nanoparticle were dispersed into 5 ml of PBS buffer (pH: 4.5). Addition of EDC (at molar ratio of FA to EDC:1:10) started FA conjugation onto CF™647-labelling HA particle. After 24 hours, the reaction solution was dialyzed exhaustedly against DI water, and the FA receptor-targeting probe was collected and dried for future use. Conjugation efficiency of the FA is estimated to be 0.12 micromole per milligram of the dried HA particle using UV-vis spectrometer.

FIGS. 4A and 4B shows an in vitro assessment of FA receptor-targeting probe to detect inflamed cells. FIG. 4A shows an increased fluorescent intensity of FA receptor-targeting probe on LPS-treated activated macrophages by control with naïve cells. FIG. 4B is a plot showing the linear relationship between cell-associated fluorescent intensity and the number of activated macrophage. Synovial macrophages play a crucial role in mediating inflammation and cartilage injury at early stage of arthritis. The previous investigations have shown that these activated macrophages surrounding cartilages are involved in the generation of osteoarthritis-like pathology. In addition, activated macrophages are known to express FA receptor. We thus believe that the measurement of FA receptor-expression cells on cartilage at the intra-articular space would provide a direct mean to diagnose early-stage arthritis. To test this hypothesis, we use FA receptor-targeting probes (FA-conjugated HA particles) and Murine Raw 264.7 Macrophages. LPS treatment (1.0 μg/ml for 4 hours) was used to activate macrophages while PBS medium was used as the control. Naïve and activated macrophages (6.0×10$^6$/well) were incubated with CF™647 dye-labeling FA receptor-targeting probes (0.1 mg/ml) for one hour @ 37° C. After washed with PBS 3×, the accumulation of FA receptor-targeting probe on cell surfaces was observed using fluorescent microscope and cell-associated fluorescent intensities were recorded using plate reader. By measuring cell-associated fluorescent intensities, we find that LPS-treated macrophages are associated with large number of FA receptor-targeting probe (FIG. 4A). Quantitative analysis further reveals that fluorescent intensity from LPS-treated macrophages is ~1.5 times higher than that from PBS-treated ones (FIG. 4B). The results show that presence of FA enhances affinity of HA particles to the activated macrophages due to the up-regulation of folate receptors upon macrophage activation. Furthermore, by incubating FA receptor-targeting probe with various numbers of activated macrophages, a linear relationship between number of the activated Macrophages and fluorescent intensity can be observed (FIG. 4B). These results show that FA receptor-targeting probe can be used to quantify the number of activated MΦ in vitro.

Figure 5:
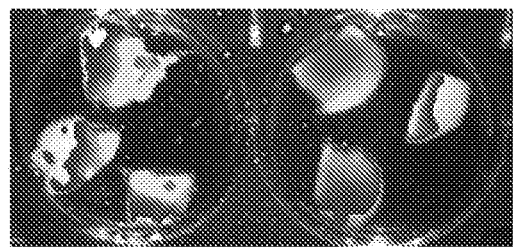
FIG. 5 is an image showing the assessment of FA receptor-targeting probes to diagnose arthritic tissue. Following incubation with the probes, we find that significant higher probe accumulation on arthritic tissue (left) than on healthy tissue (right).

FIG. 5 is an image showing the assessment of FA receptor-targeting probes to diagnose arthritic tissue. Following incubation with the probes, we find that significant higher probe accumulation on arthritic tissue (left) than on healthy tissue (right). Furthermore, discarded human articular cartilage recovered during total knee replacement was employed to explore the ability of FA receptor-targeting probe to diagnose arthritic cartilage tissue. Both diseased cartilage and healthy tissue were isolated from the discarded tissue without the link to patients' identify. As expected, FA receptor-targeting probes have higher affinity to arthritic tissue (FIG. 5 left) than those on healthy tissue (FIG. 5 right). These findings support that FA receptor-targeting probe can be used to diagnose arthritic cartilage tissue (with intense dye-associate fluorescence) and identify the area of arthritic cartilage for localized and targeted treatment.

Diagnosing arthritic cartilage by intra-articular injection of imaging probes. There is no imaging probe developed to diagnose the damage or injury on cartilage surface inside the joint. All of the previous probes were developed to detect arthritis by injecting and/or delivering the probes via blood stream. Those methods can only detect the inflammatory responses nearby the blood vessel at the bone/cartilage interface. Since cartilage tissue has almost no blood vessel, current methods thus cannot be used to assess the extent of the cell injury on the surfaces of the cartilage tissue inside the joints. Our probes are designed to diagnose the injury and damage on the surfaces of cartilage tissue. To ensure that the probes will only target injured cartilage surface tissue, the probes are designed for intra-articular injection with all components which are either derived from synovial fluid or biocompatible to synovial cells.

HA particles were fabricated as the base of the probe. Briefly, the aqueous phase was prepared by dissolving HA (60 mg, 700K) in a 3 ml of NaOH (0.2 M) solution; the organic phase was prepared by dissolved 0.2 M Aerosol OT and 0.04 M 1-heptanol in isooctane (50 ml). The aqueous solution was added dropwise into the organic phase and then the mixture was immediately homogenized for 10 minutes. Vinyl sulfone (100 μl) was subsequently added to the microemulsion and the mixture was homogenized again to disperse DVS. The reaction was allowed to proceed for 1 hour at ambient temperature with vigorous stirring. HA particles were collected by precipitation in acetone. The precipitated HA particle pellet was re-dispersed into DI water, followed by centrifugation at 1000 rpm for 10 min to remove micro-size HA. Finally, the HA nanoparticles was collected by centrifugation of the supernatant at 5000 rpm. The collected HA nanoparticles were thoroughly washed with water, ethanol and acetone before being dried at 37° C. overnight. Different formulations were used to study the effect of several parameters on particle size, viscosity, and slow-release property: molecular weight of HA, and cross-linking density (ratio of HA hydroxyl groups to vinyl groups of DVS) and HA concentration.

Figure 6A:
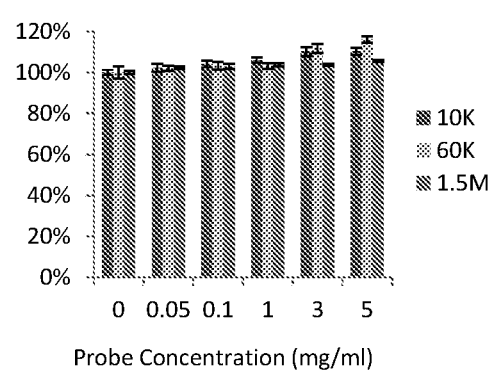
FIGS. 6A and 6B are plots that show in vitro cell toxicity of HA particles-based probes showing the effect of HA molecular weight (FIG. 6A Crosslinking density: 1:1); Effect of crosslinking density (FIG. 6B Molecular weight: 60k).
Figure 6B:
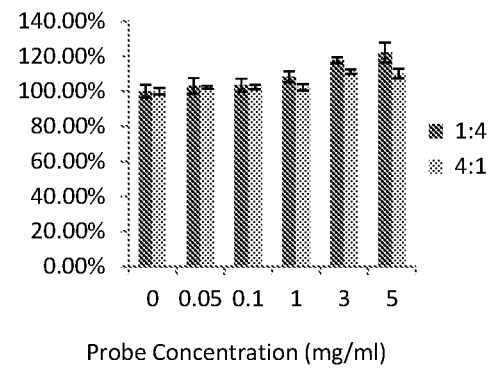

FIGS. 6A and 6B are plots that show in vitro cell toxicity of HA particles-based probes showing the effect of HA molecular weight (FIG. 6A Crosslinking density: 1:1); Effect of crosslinking density (FIG. 6B Molecular weight: 60k). The toxicity of these HA particles-based probes was investigated in vitro and in vivo. In in vitro tests, the cell toxicity of HA particles was evaluated on human chondrocytes using Alamar Blue assay. Briefly, seeded cells (5000 cells per well) were incubated with different concentrations of probes prepared under different condition in the presence of Alamar Blue for 24 hours. We find that the probes prepared with either different molecular weight or crosslinking density showed no apparent toxicity to cells with concentration up to 5 mg/ml. Similar experiments had been conducted on rabbit synoviocytes and showed the same trends as did on human chondrocytes. These results suggest that the HA particles-based probes have good cell compatibility.

To evaluate the tissue compatibility of HA particle-based probes, in vivo testing was carried out using mice subcutaneous implantation model and mice intra-articular injection model. For mouse subcutaneous implantation model, various HA particles as well as PLAG particles served as a control were implanted subcutaneously in Balb/c mice (male, about 20 g body weight) from Taconic Farms (Germantown, NY, USA). Briefly, particles (6 mg/100 µl per mouse) were administrated into subcutaneous space on the back. After implantation for 3 and 14 days, the implants and surrounding tissues were recovered, frozen sectioned, and then histological analyses. Inflammatory cell infiltration and capsule thickness served as biomarkers for assessing the extent of tissue reactions to different probes. We find that independent of molecular weight or crosslinking density, biocompatibility of all HA particle-based probes is comparable to or even better than that of PLGA particles. PLGA is a FDA-approved material and therefore these as-prepared HA particles may be used in in vivo studying of animal.

Figure 7A:
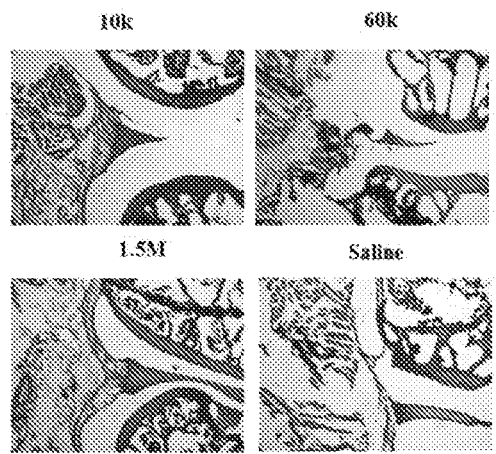
FIGS. 7A and 7B are images of HA particle-based probes trigger minimal toxicity to tissues in mouse intra-articular injection model, H&E staining (FIG. 7A) and inflammatory cell counts (FIG. 7B).
Figure 7B:
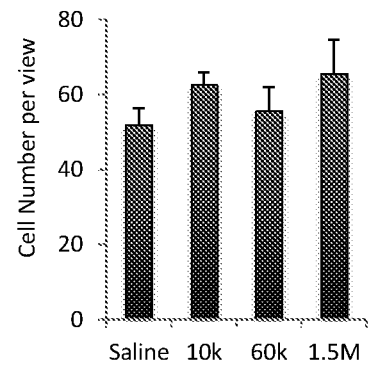

FIGS. 7A and 7B are images of HA particle-based probes trigger minimal toxicity to tissues in mouse intra-articular injection model, H&E staining (FIG. 7A) and inflammatory cell counts (FIG. 7B). Further, tissue responses to HA particle-based probes were carried out using a mouse intra-articular injection model. We find that all the probes we prepared show no/minimal toxicity to joint's tissues. Representative results are shown in FIGS. 7A and 7B. From H&E staining, the probes prepared with various molecular weight trigger similar inflammatory cell recruitment as saline does. Taking in vitro and in vivo results together, we can draw a conclusion that the HA particle-based probes are safe to cells and tissues.

Figure 8A:
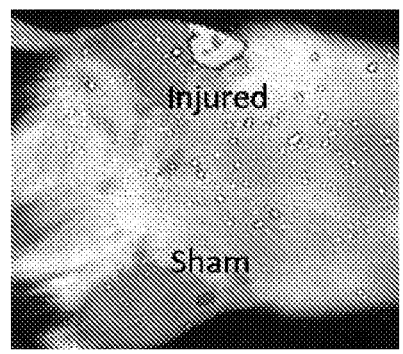
FIG. 8A and 8B are in vivo imaging of rat cartilage injury and its quantification analysis, respectively. The data support that the HA particle-based probes (CD44-targeting probes) have higher affinity to mechanical trauma injured cartilage than to control (healthy cartilage).
Figure 8B:
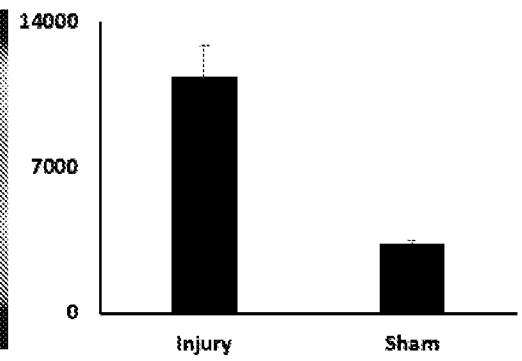

FIG. 8A is in vivo imaging of rat cartilage injury and its quantification analysis (FIG. 8B). The data support that the HA particle-based probes (CD44-targeting probes) have higher affinity to mechanical trauma injured cartilage than to control (healthy cartilage).

Finally, cartilage injury rat model was employed to investigate whether the particle probe can be used to detect cartilage injury in vivo. First, femur cartilage injuries in left knees of rats (n=3) were created using a 22 G needle while right knees leave non-injured as controls. 100 µl of HA particle-based probes (1 mg/ml) was intra-articularly injected. After 30 minutes, in vivo imaging was captured using a Kodak in vivo imaging system and the results are presented in FIG. 8. One can observe that strong fluorescent signal is associated with the mechanically injured cartilage while very weak signal is visualized in control knee (FIG. 8A). Quantification analysis shows an approximate 4× higher particle accumulation in the injured cartilage (FIG. 8B). The results support that the HA particle-based probe (CD44-targeting probes) can be administered intra-articularly to detect cartilage injury in vivo. Our probe can detect injured and damaged cartilage without going through blood stream.

Probes with degradable property. To ensure the safety of human use and to avoid potential foreign body reactions, the arthritis diagnosing probes are designed to possess biodegradable properties by fabricating the probes using biodegradable materials. The probes are fabricated using different biodegradable materials, including hyaluronic acid (HA), polyethylene glycol, chitosan particles, gelatin particles, collagen particles, albumin particles, PLGA/PLA particles and polyethylene glycol nanoparticles etc.

Figure 9A:
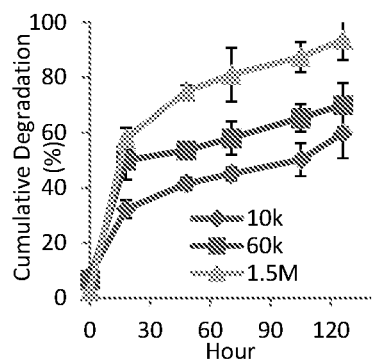
FIGS. 9A and 9B show the in vitro degradation of HA particle-based probes. Effect of HA molecular weight (FIG. 9A Crosslinking density: 1:1); Effect of crosslinking density (FIG. 9B Molecular weight: 60k).
Figure 9B:
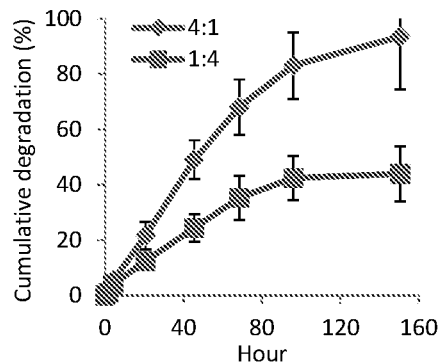

FIGS. 9A and 9B show the in vitro degradation of HA particle-based probes. Effect of HA molecular weight (FIG. 9A Crosslinking density: 1:1); Effect of crosslinking density (FIG. 9B Molecular weight: 60k). The degradation of the as-prepared HA particle-based probes was tested in the presence of hyaluronidase (50 units/ml) in vitro. One can observe that degradation profiles of HA particle-based probes in presence of hyaluronidase depended on either HA molecular weight or crosslinking density. The HA probes prepared with higher molecular weight degraded faster than those prepared with lower molecular weight, and increasing crosslinking density decreased degradation rate of HA particle-based probes. This may be because HA particle-based probes made with higher molecular weight or lower crosslinking density shows higher swelling ratio, which allows enzyme to more easily penetrate into microscaffolds cleaving the networks. These results support that our imaging probes can be degradable inside the body and there is no risk of accumulation of our probes inside the body following multiple-injections.

Probes for quick detection (<15 minutes). The arthritis diagnosing probes are designed to provide quick disease diagnosis. To do so, the probes are designed to have high affinity to diseased cartilages and to provide quick visualization of the disease tissue. Currently, there is no imaging probe which can be used to detect cartilage injury and damage for less than 12 hours. To overcome this drawback, our probes are developed to be administered inside the joint and be circulated in the synovial fluid and finally to accumulate on the surfaces of the injured cartilage. For that, we have selected hyaluronic acid (HA) as the component of the probe, since HA is one of the main component in the synovial fluid.

Figure 10A:
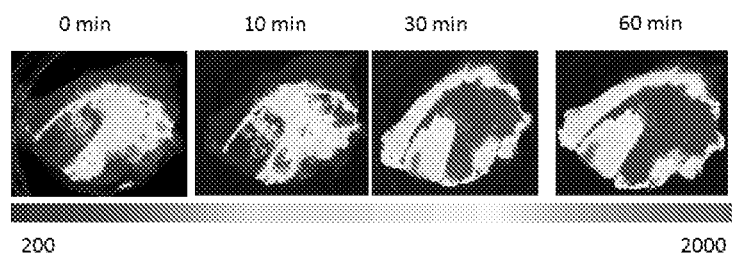
FIG. 10A shows ex vivo CD44-targeting probes can be used to quickly identify the area of cartilage tissue injury and damages by preferentially accumulate at the area of injured cartilage tissue.
Figure 10B:
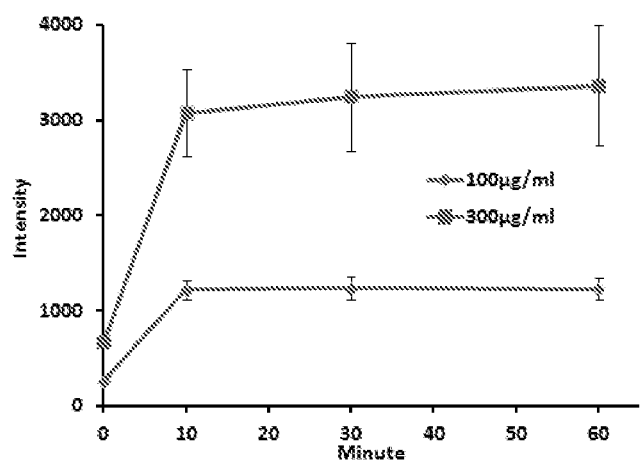
FIG. 10B is a graph of the amount of probe accumulated on arthritic cartilage were quantified at different time points.

FIG. 10A shows ex vivo CD44-targeting probes can be used to quickly identify the area of cartilage tissue injury and damages by preferentially accumulate at the area of injured cartilage tissue. FIG. 10B is a graph of the amount of probe accumulated on arthritic cartilage were quantified at different time points. The ability of HA particle-based probes (CD44-targeting probes) to diagnose arthritic cartilages was investigated. For that, the human arthritic cartilage tissues were placed in a 6-well plate. For each well, a 6 ml of DMEM media containing CF™647 dye-labelling CD44-targeting probes (Final concentration: 100 or 300 µg/ml) was added into the well plate and incubated at 37° C. At various time points, the well plated was placed in a portable near infrared imaging system to record fluorescent intensity of tissues (excitation: 630 nm; emission: 700 nm). The results are shown that, regardless of probe concentration, the CD44-targeting probes can quickly accumulated in the arthritic cartilage tissues—top right corner of the tissue (FIG. 10A). Incubation after 10 min, there is no significant increase in fluorescent intensity over time. At this time point, the arthritic cartilage tissue triggers approximately 3 times higher probe accumulation than the healthy tissues. Similar results were observed for folate receptor-targeting probes. Overall, our results have shown that our probes can be used in quick identify the areas of the arthritic cartilages (<15 minutes).

Figures 11A, 11B:
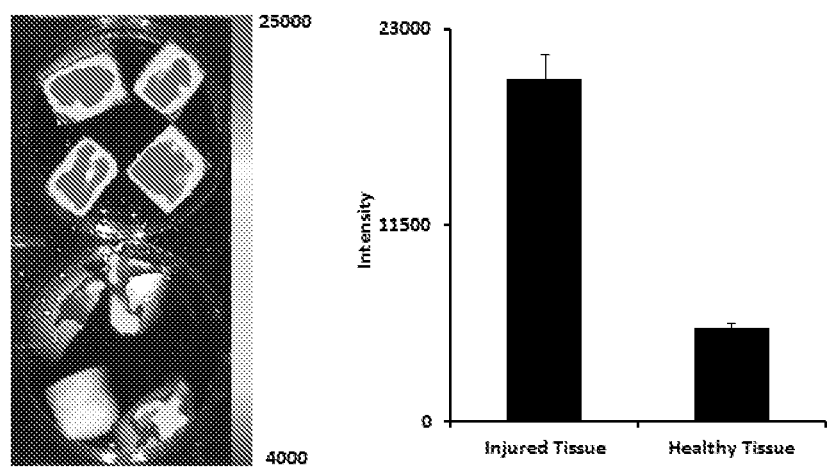
FIGS. 11A and 11B show the diagnoses of mechanically injured cartilages using FA receptor targeting probes.

FIGS. 11A and 11B show the diagnoses of mechanically injured cartilages using FA receptor targeting probes. FIG.

11A is an image that shows the FA receptor-targeting probes are preferentially accumulate on mechanically injured tissue (top) than healthy tissue (bottom). FIG. 11B is a graph of the amounts of probe accumulated on both injured and healthy tissue were quantified and then compared (right).

Probes for mechanical or compression trauma. Arthritis can be caused by different mechanisms. Although some detection methods have been developed for joint inflammation, there is no method developed for detecting cartilage injuries caused by mechanical and/or compression trauma. To overcome such gap, the probes developed here are designed to target CD44 and/or folate receptors which are the hallmark of mechanical and/or compressional injured cartilages.

Healthy cartilage in human joints suffers repeatedly from up to as high as 15-20 MPa normal mechanical impact in vivo. Higher physical impact may lead to tissue injury and eventually cause cartilage degradation. Early detection of the cartilage injury is crucial to prevent irreversible cartilage degradation using non-surgical treatment. An in vitro model of mechanically-injured bovine cartilage explants, according to previous studies, was employed to investigate if the FA receptor-targeting probe can be used to detect cartilage injury generated by the mechanical load. Briefly, cartilage explant disks (8×4 in mm, 1-mm thickness) were obtained from femoropatellar groove of 2-week-old bovine calves. After cartilage explants were cultured for 7 days in DMEM culture medium. Among them, some explants were used to generate the injured explants by clamping the explants using hemostat or placing stainless rod on top of the cartilage tissue with 14-20 MPa for 2.0 mins. Mechanically injured tissue and control healthy tissues were placed into the wells of a 6-well plate containing a 3 ml of DMEM per well (CF™647 dye-labelling FA receptor-targeting probe, 0.4 mg/ml) for 15 minutes hours at 37° C. Finally, ex vivo imaging of these tissues were captured using a portable imager. The results are shown that much stronger fluorescence intensity is observed from the injured tissue than from non-injured tissue (FIG. 11A). Mechanical impact to cartilage explants triggers approximately 4 times higher FA receptor-targeting probe accumulation (FIG. 11B). Similar results are observed for CD44 receptor-targeting probes. These results claim that both FA receptor-targeting probe and CD44-targeting probes can be used to detect mechanical impact-associated cartilage injury.

FIG. 12A-12C diagnose of mechanically injured xiphoid using CD44 targeting probes. FIG. 12A shows CD44-targeting probes accumulated on mechanically injured cartilage but not healthy one (top). The amounts of probe accumulated on both injured and healthy tissue were quantified and then compared (bottom). FIG. 12B shows the ex vivo result and FIG. 12C shows quantifies the fluorescence. The ability of CD44-targeting probes to detect mechanical injured cartilage was tested using an established xiphoid injury model. The xiphoid was injured with hemostat compression at 14-20 MPa for 2.0 mins. After injured for 24 hours, the CD44-targeting probes were injected into the peritoneal space (a close space without circulating blood). After probe injection for 24 hours, the animals were then imaged using Kodak in vivo Imaging system. Our results have found that the CD44-targeting probes can diagnose mechanically injured cartilage tissue inside a live animal.

Probes for small injury (1 mm or larger). No method has been developed thus far to detect and then to treatment early stage of arthritis which is associated with a small area of injured or damaged cartilage. Our probes are designed to diagnose early stage of arthritis which are often caused by small and localized injured on the cartilage via mechanical or compression forces. The mechanical force will cause cell injury and activation to express different extent of CD44 receptor and/or folate acid (FA) receptor. By identifying the area with high level of CD44 receptor or FA receptor, our probes can be used to identify a very small and localized mechanical or compression force-induced injury.

FIG. 13A is an image and FIG. 13B is a plot quantification of 1 mm diameter-sized cartilage injury. CD44-targeting HA-based probes were found to preferentially accumulate at the injured site. CD44 receptor-targeting probes (with CF™647 dye labeling) were used to detect cartilage surface injury caused by stainless steel rod (1 mm diameter) with 20 MPa for 2 minutes. The probe solution (0.4 mg/ml) was then placed on top of whole tissue for 15 minutes. The fluorescent images of the tissue were then recorded using a portable imager. We find that strong fluorescent signal can be observed in the injured site of cartilage. Our results have shown that our probe was able to detect injuries as small as 1 mm diameter on cartilage surfaces. This capability allows us to deliver the treatment only to the area of the injured cartilage for improved therapeutic outcomes.

Probes for surface molecules without minimal internalized (>200 nm). All of the existing probes are fabricated in nanometer size (<100 nm). Unfortunately, probes with such small size can be easily internalized by cells. This property will affect the accuracy of injury diagnosis, since it would be difficult to distinguish whether the accumulation of the probes is caused by cell surface targeting or cell internalizations. To overcome such drawback, our probes are fabricated in sub-micrometer size which have substantially lesser chance to be internalized (or eaten by the cells).

We used chelator (EDTA) to release the particle:cell receptor interactions. However, once that the probes are internalized by the cells, such treatment cannot wash the probe away and the cell will retain the probes' fluorescent intensities.

Figure 14:
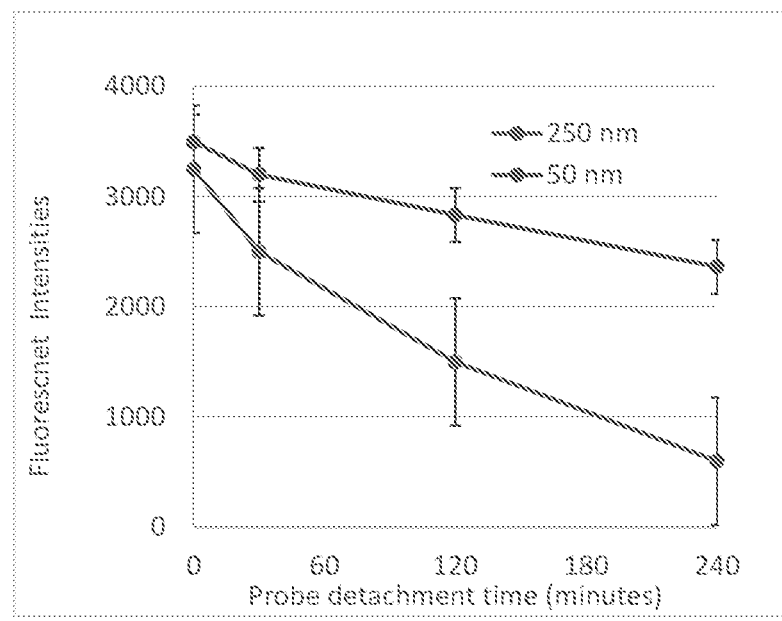
FIG. 14 is a graph of the influence of the sizes of CD44-targeting probes on their chance to be internalized. Our data find that probe >250 nm accumulate on arthritic tissue mostly via receptor interactions. However, small probes (such as 50 nm diameter) accumulated on arthritic tissue via internalization which cannot be removed with EDTA wash.

FIG. 14 is a graph of the influence of the sizes of CD44-targeting probes on their chance to be internalized. Our data find that probe >250 nm accumulate on arthritic tissue mostly via receptor interactions. However, small probes (such as 50 nm diameter) accumulated on arthritic tissue via internalization which cannot be removed with EDTA wash. The human arthritic cartilage tissues were placed in a 6-well plate. For each well, a 6 ml of DMEM media containing two different sizes of CF™647 dye-labelling CD44-targeting probes (250 nanometer diameter vs. 50 nanometer diameter) at 300 µg/ml incubated at 37° C. for 60 min. The tissue was then incubated with DMEM media with 0.05% EDTA. At various time points, the well plated was placed in a Kodak in vivo Imaging system to record fluorescent intensity of tissues (excitation: 630 nm; emission: 700 nm) and the results were shown FIG. 14.

We find that the 50 nm sized probe-incubated tissues are much better to retain their florescent intensities than 250 nm probe-incubated tissues. These results support that larger size probes can reduce the chance of internalization and have better chance for arthritis diagnosis than small sized probes. Therefore, all of our probes are fabricated with size >200 nm.

Probes for recruiting chondrocytes. Our goal is to trigger the recruitment of chondrocytes to cartilage injured sites. The presence of chondrocytes would then help to repair injured cartilage tissues and cells. Injured cartilage tissue/cells-targeting HA particle are loaded with chondrocyte-specific chemokines. By releasing at the injured tissue sites, the released chemokines will produce chemokine gradient to direct the recruitment of chondrocytes to the sites of cartilage tissue injury.

Figure 15:
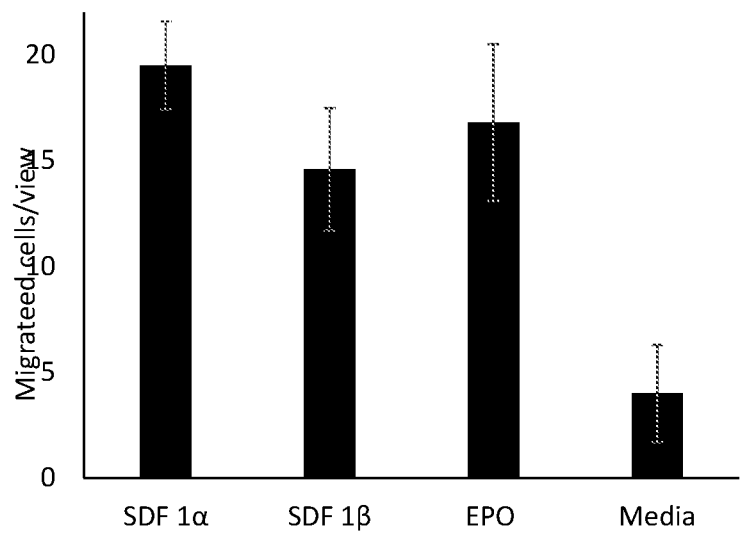
FIG. 15 is a plot showing human chondrocyte migration induced by released SDF 1, SDF 1β, and Epo.

Investigation of chondrocyte migration associated with the released biomolecule from HA scaffold. FIG. 15 is a plot showing human chondrocyte migration induced by released SDF 1, SDF 1β, and Epo. Released EPO, SDF-1α and SDF-1β was added into 700 μl of serum free chondrocyte growth media (final concentration of EPO, SDF-1α and SDF-1β:10 units/ml, 10 ng/ml and 10 ng/ml), and then the conditioned media were transferred into a bottom chamber of a transwell. $2 \times 10^5$ human chondrocytes in 200 μl of serum free chondrocyte growth media was placed into top chamber. After 24-hour incubation, migrated chondrocytes were stained with Wright-Geimsa and counted under a microscopy. The result was shown in FIG. 15. Interestingly, it was also discovered that the released chemokines can promote the migration of human chondrocytes. Quantification analysis showed that there was an approximate 4.9, 3.7 and 4.2 times higher cell migration than the control media. These results suggest that, by releasing chemokines at the site of injured cartilage cells, HA scaffolds may promote the recruitment of either stem cells, chondrocytes, or both types of cells to the injured site. This "bonus" may further enhance the regeneration of injured cartilage tissues.

Probes for recruiting stem cells. Our goal is to trigger the recruitment of stem cells to cartilage injured sites. The presence of stem cells would then help to repair injured cartilage tissues and cells. Injured cartilage tissue/cells-targeting HA particle are loaded with stem cell-specific chemokines. By releasing at the injured tissue sites, the released chemokines will produce chemokine gradient to direct the recruitment of stem cells to the sites of cartilage tissue injury.

Figure 16:
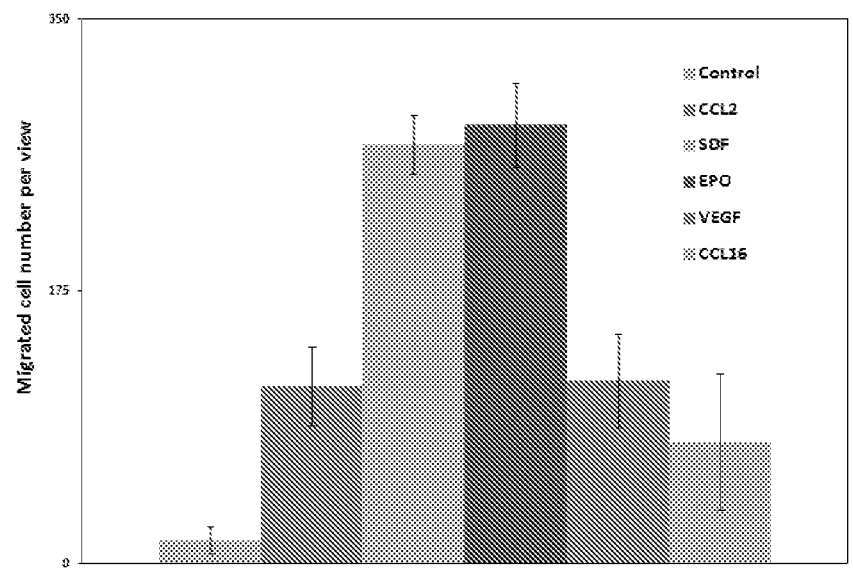
FIG. 16 is a plot showing BMSC migration induced by various growth factors and quantification analysis.

Investigation of stem cell migration triggered by various growth factors. FIG. 16 is a plot showing BMSC migration induced by various growth factors and quantification analysis. Five growth factors (SDF, EPO, VEGF, CCL2 and CCL16) were used. Through the investigation, 2-3 growth factors which can recruit the most amounts of stem cells will be selected. To do this, cell migration assay was performed using Transwell (8 μm polycarbonate, 6.5 mm inserts, Costar). Human bone marrow stromal cells (BMSCs) were washed thrice with PBS and then plated overnight in RPMI. In all experiments, $5 \times 10^4$ cells were re-suspended in RPMI (100 μl) and respectively incubated with rHuEPO (100 units/ml), CCL2 (30 ng/ml), CCL16 (30 ng/ml), SDF (9 ng/ml) and VEGF (0.8 μg/ml). Cells were added to the top of each migration chamber and allowed to migrate to the underside of the chamber for 14 h in the presence of 10% FCS in the lower chamber. The upper surfaces of the filters were wiped clean of cells and the filters were then fixed by immersion in 100% methanol and stained with Giemsa for 15 mins. The migrated cells were captured using bright-field microscopy. Migrated cells from the captured image were counted using ImageJ software. The results were shown in App.16. One can observe that EPO and SDF trigger much more BMSC migration than CCL16, CCL2 and VEFG. Quantification analysis shows that compared to control, CCL16, CCL2, VEGF, SDF and EPO trigger 5.2, 7.6, 7.8, 18 and 19 times higher cell migration, respectively. Therefore, EPO and SDF (1α and 1β) are able to be used to recruit cell migration.

Figure 17:
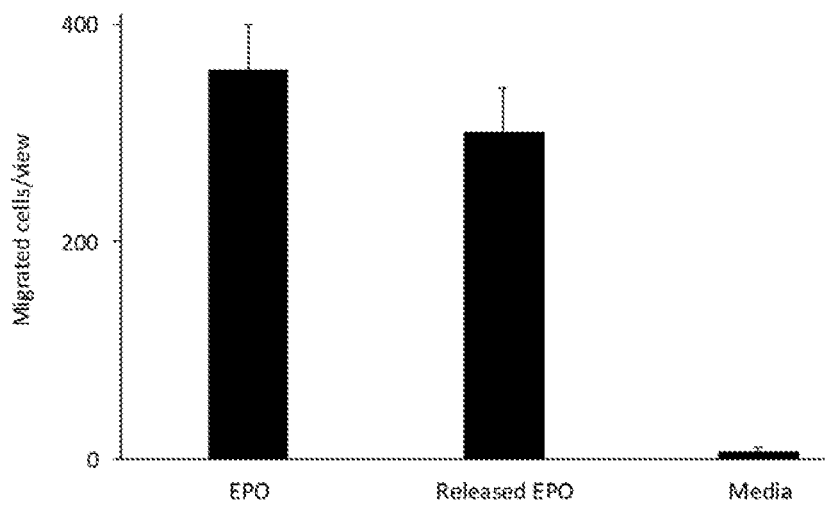
FIG. 17 is a plot of the BMSC migration induced by control EPO, EPO released from HA particles and media, respectively.

Investigation of stem cell migration associated with the released biomolecule from HA scaffold. FIG. 17 is a plot of the BMSC migration induced by control EPO, EPO released from HA particles and media, respectively. The biomolecules were loaded into HA scaffolds in two ways: physical adsorption and chemical conjugation. For physical adsorption, 1 mg of HA scaffolds (500 nm in diameter) was incubated with 7 μg of EPO in 200 μl of PBS buffer overnight at 4° C. The supernatant was collected by centrifugation and the amount of free EPO was measured to determine loading efficiency of EPO. For chemical conjugation, 1.0 mg of the HA scaffolds (500 nm in diameter) and 7 μg of EPO was sequentially dispersed into 200 μl of PBS buffer (pH:4.5), and then 1-ethyl-3-(3-dimethylaminopropyl) carbodiimide hydrochloride (EDC) (at molar ratio of EPO to EDC:1:10) was added into the mixture to initiate EPO conjugation into HA scaffolds. After 24-hour incubation, the EPO-loaded HA scaffolds were purified with exhausting dialysis against DI water. SDF-1α/SDF-1β-loaded HA scaffolds were also prepared using the similar method.

As an example, EPO-loaded HA particles were used to trigger stem cell migration. For the purpose, EPO was loaded into HA particles by physical method. 0.1 mg of HA particles containing 200 units of EPO was added into RPMI media, and then the EPO-loaded HA media was incubated for 2 days at 37° C. The supernatant was collected by centrifuge and used for stem cell migration study via transwell migration assay. Fresh EPO (200 units) and media were used as controls. The result was shown in App.17. One can observe that the released EPO can trigger stem cell migration although there is a slight reduction (~8%) on migrated stem cells relative to fresh EPO. This reduction of migrated stem cells may be due to incomplete EPO release from HA particles.

Scaffolds for directing chondrogenic differentiation. It is well established that stem cells can be differentiated into chondrocytes using different agents/cocktails. By release chondrogenic agents at the cartilage injured sites, injured cartilage-targeting probes are made to promote chondrogenic differentiation of recruited stem cells. Injured cartilage-targeting probes are loaded (physically or chemically) with chondrogenic differentiation agents to create the chondrogenic differentiation microenvironment to promote the differentiation of recruited stem cells into chondrocytes.

Figure 18A:
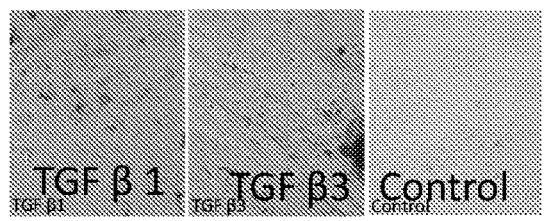
FIG. 18A is an image of the BMSC differentiation triggered by released TGF β1 and TGF β3 and FIG. 18B is its quantification analysis.
Figure 18B:
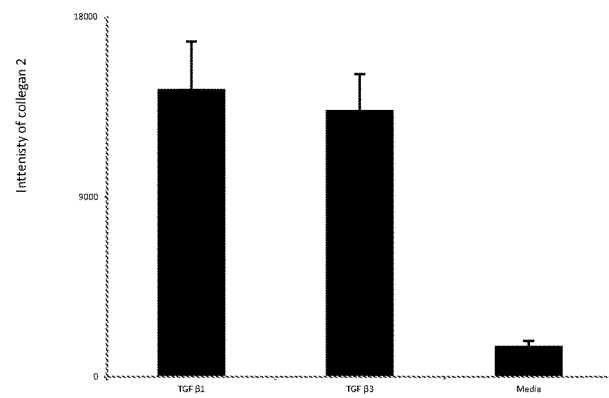

Investigation of stem cell differentiation associated with the released biomolecule from HA scaffold. FIG. 18A is an image of the BMSC differentiation triggered by released TGF β1 and TGF β3 and FIG. 18B is its quantification analysis. Further studies were also conducted to evaluate the ability of the chemokine-loaded HA scaffolds to accelerate chondrogenic differentiation of migrated stem cells. Migrated BMSCs were incubated with culture media as controls, TGF-β1 and TGF-β3 at concentration of 20 ng/ml released from HA (500 nm in diameter) After culturing for 3 weeks, the extent of cartilage matrix formation was then quantitatively analyzed using toluidine blue staining. The result was shown in FIG. 18. TGF-β1 triggers slightly higher chondrogenic differentiation of stem cells than TGF-β3. These results showed that, by releasing chemokine agents like TGF-β1 and TGF-β3, cartilage or synovial stem cells can migrate to the injured cartilage and regenerate the tissue.

Figure 19A:
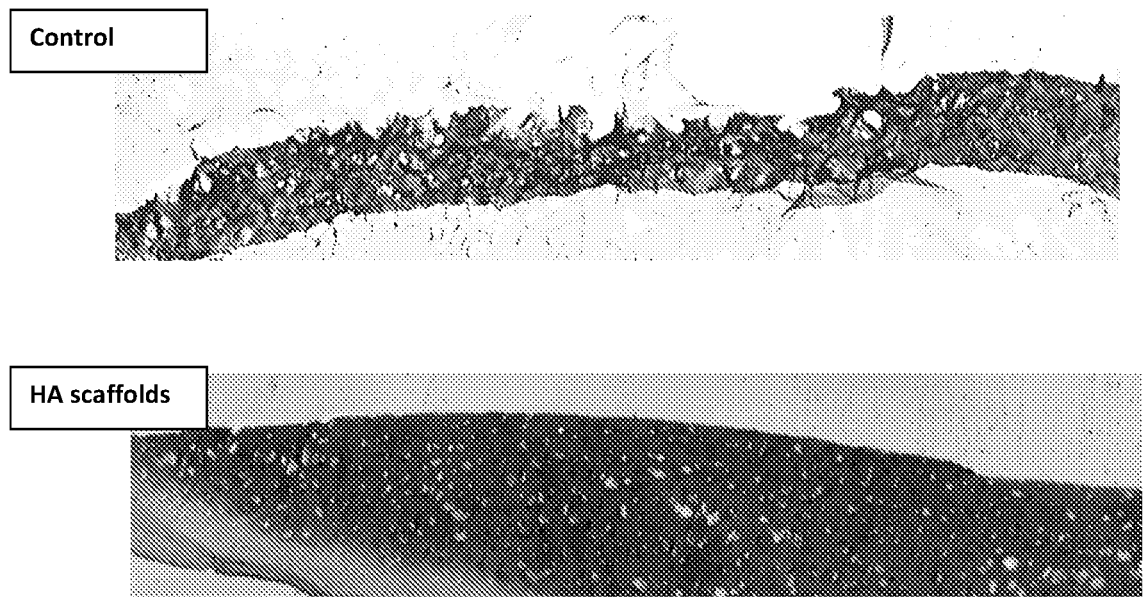
FIG. 19A is an image of human arthritic cartilage without treatment and with treatment of HA scaffolds/probe.
Figure 19B:
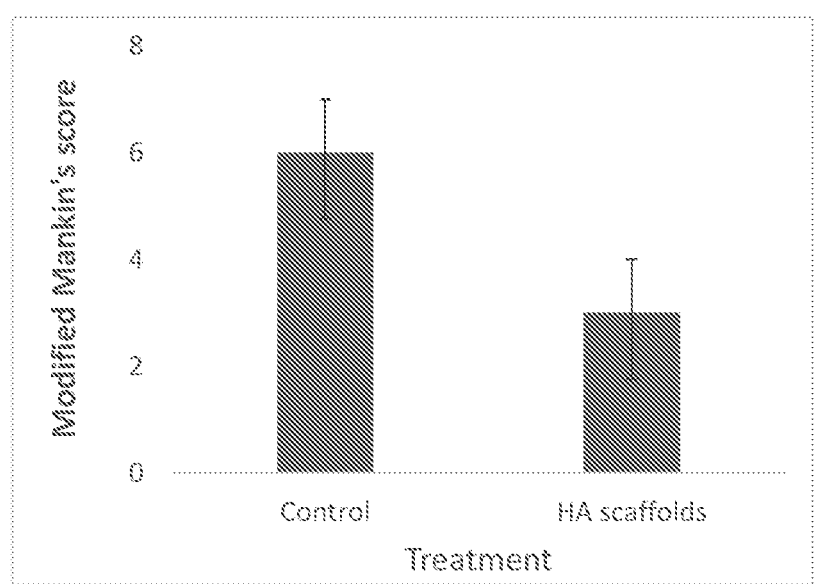
FIG. 19B is a plot of the Modified Mankin's score of the arthritic cartilage with or without HA scaffold treatment in vitro for 2 weeks.

Investigation of injured cartilage-targeting HA scaffolds on cartilage tissue regeneration. Arthritic cartilage tissue was incubated with HA particle scaffolds for a period of 2 weeks. The tissue was then sectioned and stained for Safranin-O. The extent of cartilage injury was then quantified based on the Modified Mankin's classification system. FIG. 19A is an image of the control injured tissue and an image of HA particle treated injured tissue. The images show that the treatment of HA particles can promote the regeneration of the cartilage cells and tissue. The Modified Mankin's score (FIG. 19B) supports that HA scaffold treatment significantly reduce cartilage injured, perhaps, by triggering cartilage regeneration. It is likely that the accumulation of injured cartilage-targeting HA particle scaffolds may promote the immigration of chondrocytes migrated from surrounding healthy tissue to the injured site.

Figure 20A:
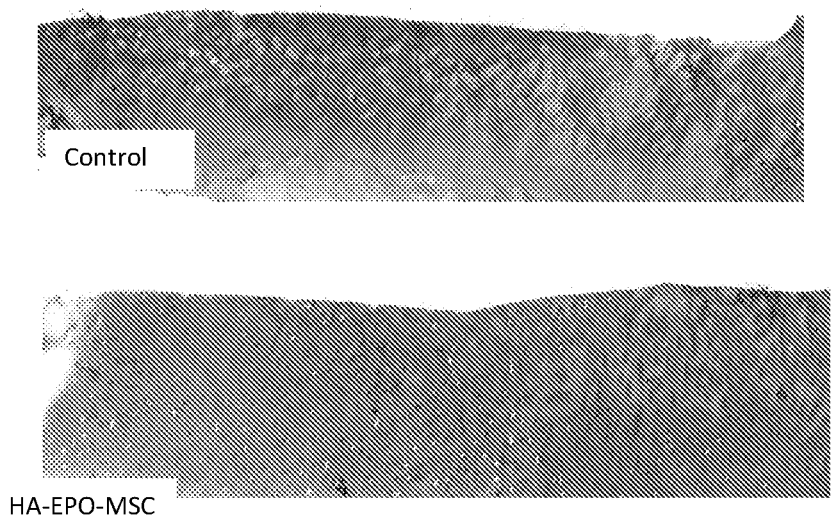
FIG. 20A is an image of human arthritic cartilage without treatment and with treatment of Epo-loaded HA scaffolds and mesenchymal stem cells.
Figure 20B:
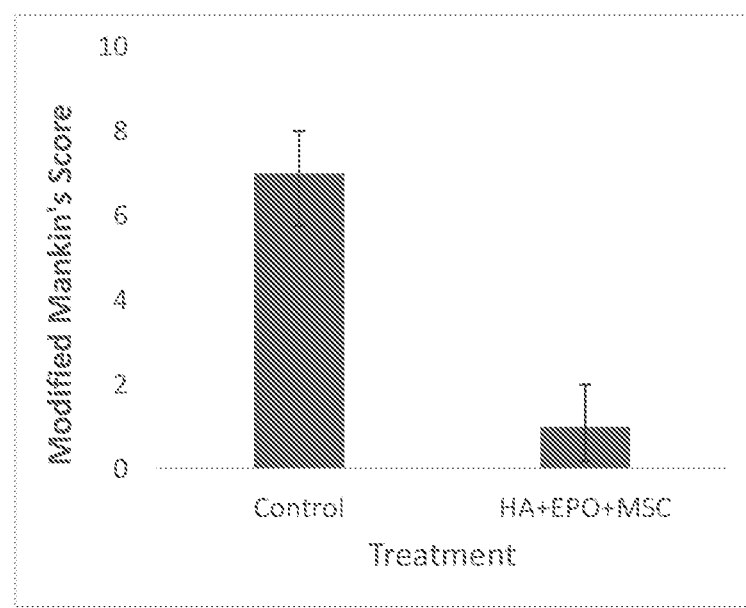
FIG. 20B is a plot of the Modified Mankin's score of the arthritic cartilage without treatment vs with treatment of Epo-loaded HA scaffolds and mesenchymal stem cells in vitro for 2 weeks.

Investigation of injured cartilage-targeting HA scaffolds loaded with EPO and incubated with mesenchymal stem cells (MSCs) on cartilage tissue regeneration. Arthritic cartilage tissue was incubated with HA particle scaffolds for a period of 2 weeks. The tissue was then sectioned and stained for Safranin-O. The extent of cartilage injury was then quantified based on the Modified Mankin's classification system. FIG. 20A is an image of the control injured tissue and an image of HA particle treated injured tissue. The images show that the treatment of HA particles can promote the regeneration of the cartilage cells and tissue. The Modified Mankin's score (FIG. 20B) supports that the combined treatment of EPO-loaded HA scaffold and MSCs drastically reduced cartilage injured, perhaps, by triggering stem cell-mediated cartilage regeneration. It is likely that HA particle scaffolds may target injured cartilage and then release EPO which lead to MSCs accumulation on injured cartilage. As the results, the treatment significantly improve chondrocyte responses of stem cells and then cartilage regeneration.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

The invention claimed is:

1. An arthritic cartilage targeting probe comprising:
a biocompatible hyaluronic acid polymer crosslinked by a vinyl sulfone to form a crosslinked biopolymer, wherein the biocompatible hyaluronic acid polymer has a molecular weight of 10K to 1.5M and the crosslinking ratio of the biocompatible HA polymer:vinyl sulfone is between 4:1 and 1:4 and the crosslinked biopolymer has a diameter of about 200 to 500 nm to modulate internalization;
a ligand in contact with the crosslinked biopolymer, wherein the ligand is hyaluronic acid that interacts with a CD44 receptor, folic acid that interacts with a folate receptor or both; and
a detectable tag in contact with the crosslinking agent, first biocompatible polymer, the ligand or a combination thereof, wherein the probe triggers stem cell recruitment, differentiation, and cartilage regeneration.

2. A damaged cartilage targeting probe comprising:
a biocompatible hyaluronic acid polymer crosslinked by a vinyl sulfone to form a crosslinked biopolymer, wherein the biocompatible hyaluronic acid polymer has a molecular weight of 10K to 1.5M and the crosslinking ratio of the biocompatible HA polymer:vinyl sulfone is between 4:1 and 1:4 and the crosslinked biopolymer has a diameter of about 200 to 500 nm to modulate internalization;
a ligand in contact with the crosslinked biopolymer, wherein the ligand interacts with one or more cell surface targets; and
a detectable tag in contact with the crosslinking agent, first biocompatible polymer, the ligand or a combination thereof, wherein the probe triggers stem cell recruitment, differentiation, and cartilage regeneration.

3. A method for identifying damaged cartilage comprising:
providing a damaged cartilage targeting probe that comprises a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4; wherein the crosslinked biopolymer has a diameter of about 200 to 500 nm to modulate internalization; a ligand in contact with the crosslinked biopolymer, wherein the ligand interacts with one or more cell surface targets; and a detectable tag in contact with the crosslinking agent, first biocompatible polymer, the ligand or a combination thereof;
contacting a cartilage suspected of being damaged with the damaged cartilage targeting probe; and
detecting the damaged cartilage targeting probe.

4. A cartilage targeting probe to treat damaged cartilage by recruiting stem cells, chondrocytes or both to the damaged cartilage, wherein the cartilage targeting probe comprises:
a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4 and the crosslinked biopolymer has a diameter of about 200 to 500 nm to modulate internalization;
a ligand in contact with the crosslinked biopolymer, wherein the ligand interacts with one or more cell surface targets;
one or more chemokines selected from SDF 1, SDF 1β, Epo, CCL2, CCL16, VEGF, TGF-β1 and TGF-β3, associated with the polymer targeting probe, wherein the one or more chemokines are released to recruit stem cells, chondrocytes or both; and a detectable tag in contact with the crosslinking agent, first biocompatible polymer, the ligand or a combination thereof.

5. A cartilage targeting probe to treat damaged cartilage by increasing chondrogenic differentiation, wherein the cartilage targeting probe comprises:
  a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4 and the crosslinked biopolymer has a diameter of about 200 to 500 nm to modulate internalization;
  a ligand in contact with the crosslinked biopolymer, wherein the ligand interacts with one or more cell surface targets;
  one or more TGF active agents selected from TGF-β1 and TGF-β3 associated with the polymer targeting probe, wherein the one or more TGF active agents are released to trigger higher chondrogenic differentiation; and
  a detectable tag in contact with the crosslinking agent, first biocompatible polymer, the ligand or a combination thereof, wherein the probe triggers stem cell recruitment, differentiation, and cartilage regeneration.

6. The arthritic cartilage targeting probe of claim 1, wherein the ligand is hyaluronic acid and the one or more cell surface targets is a CD44 receptor.

7. The arthritic cartilage targeting probe of claim 1, wherein the ligand is a folic acid and the one or more cell surface targets is a folate receptor.

8. The arthritic cartilage targeting probe of claim 1, wherein the damaged cartilage is from mechanical trauma, physical trauma compression trauma, arthritic damage, inflammatory damage or a combination thereof.

9. The arthritic cartilage targeting probe of claim 1 wherein the molecular weight is about 10K, 60K, 700k, 1.5M or incremental variations thereof.

10. The arthritic cartilage targeting probe of claim 1, wherein the crosslinking ratio is 1:4, 1:3, 1:2, 1:1, 1:3.9, 1:3.5, 1:2.3, 4:1, 3:1, 2:1 and incremental variations thereof.

11. The arthritic cartilage targeting probe of claim 1, wherein the detectable tag is a fluorescent dye, a radioactive tag, a metal, a nanoparticle or a combination thereof.

12. The arthritic cartilage targeting probe of claim 1, wherein the polymer targeting probe is biodegradable.

13. The arthritic cartilage targeting probe of claim 4, wherein the one or more chemokines or one or more TGF active agents are bound to the crosslinked biopolymer, releasably associated, disposed in the crosslinked biopolymer, spray coated on the crosslinked biopolymer or a combination thereof.

14. The arthritic cartilage targeting probe of claim 4 wherein the crosslinked biopolymer comprises one or more pores and the one or more chemokines or one or more TGF active agents are disposed in the one or more pores for extended release over time.

15. The arthritic cartilage targeting probe of claim 14, wherein the one or more pores have a diameter of 1, 2, 3, 4, 5, 6, 7, 8, 9, 10, 11, 12, 13, 14, 15, 16, 17, 18, 19, 20, 21, 22, 23, 24, 25, 26, 27, 28, 29 nm or less than 1 nm or greater than 29 nm.

16. The arthritic cartilage targeting probe of claim 1, wherein the polymer targeting probe contacts the one or more targets in less than 15 minutes to allow the quick detection within 15 minutes.

17. The arthritic cartilage targeting probe of claim 1, the polymer targeting probe is intra-articular injected.

18. The arthritic cartilage targeting probe of claim 1, wherein the targeting probe is used to image the damaged/injured cartilage and deliver one or more active agents to the damaged/injured cartilage.

19. A damaged/injured cartilage imaging probe for use as a medicament to target and/or treat damaged cartilage, wherein the damaged cartilage imaging probe comprises
  a biocompatible hyaluronic acid polymer crosslinked by a vinyl sulfone to form a crosslinked biopolymer, wherein the biocompatible hyaluronic acid polymer has a molecular weight of 10K to 1.5M and the crosslinking ratio of the biocompatible HA polymer:vinyl sulfone is between 4:1 and 1:4 and the crosslinked biopolymer has a diameter of about 200 to 500 nm to modulate internalization;
  a ligand in contact with the crosslinked biopolymer, wherein the ligand is hyaluronic acid that interacts with a CD44 receptor, folic acid that interacts with a folate receptor or both; and
  a detectable tag in contact with the crosslinking agent, first biocompatible polymer, the ligand or a combination thereof, wherein the detectable tag can be detected at the damaged cartilage and used to generate an image of the damaged cartilage, wherein the probe triggers stem cell recruitment, differentiation, and cartilage regeneration.

20. A damaged cartilage probe for use as a medicament for targeted treatment of damaged cartilage, wherein the damaged cartilage probe comprises:
  a cartilage damaged imaging probe for identifying damaged cartilage, wherein the cartilage damaged imaging probe comprises a biocompatible hyaluronic acid polymer crosslinked by a vinyl sulfone to form a crosslinked biopolymer, wherein the biocompatible hyaluronic acid polymer has a molecular weight of 10K to 1.5M and the crosslinking ratio of the biocompatible HA polymer:vinyl sulfone is between 4:1 and 1:4 and the crosslinked biopolymer has a diameter of about 200 to 500 nm to modulate internalization; a ligand in contact with the crosslinked biopolymer, wherein the ligand is hyaluronic acid that interacts with a CD44 receptor, folic acid that interacts with a folate receptor or both; and, a detectable tag in contact with the crosslinking agent, first biocompatible polymer, the ligand or a combination thereof, wherein the detectable tag can be detected at the damaged cartilage and used to generate an image of the damaged cartilage; and
  a cartilage targeting probe for use as a medicament to treat damaged cartilage by recruiting stem cells, chondrocytes or both to the damaged cartilage, wherein the cartilage targeting probe comprises: a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4 and the crosslinked biopolymer has the diameter of about 200 to 500 nm to modulate internalization; a ligand in contact with the crosslinked biopolymer, wherein the ligand interacts with one or more cell surface targets; one or more chemokines selected from SDF 1, SDF 1β, Epo, CCL2, CCL16, VEGF, TGF-β1 and TGF-β3, associated with the polymer targeting probe, wherein the one or more chemokines are released to recruit stem cells, chondrocytes or both; and optionally a second detectable tag in contact with the crosslinking agent, first biocompatible polymer, the ligand or a combination thereof; and optionally a chondrogenic differentiation probe for use as a medicament to treat damaged cartilage by increasing chondrogenic differentiation, wherein the chondrogenic differentiation probe comprises: a biocompatible hyaluronic acid polymer crosslinked by a vinyl sulfone crosslinking agent to form a crosslinked biopolymer, wherein the biocompatible hyaluronic acid polymer has a molecular weight of 10K to 1.5M and the crosslinking ratio of the biocompatible polymer:crosslinking agent is between 4:1 and 1:4 and the crosslinked biopolymer has a diameter of greater than about 200 nm to modulate internalization; a ligand in contact with the crosslinked biopolymer, wherein the ligand interacts with one or more cell surface targets; one or more TGF active agents selected from TGF-β1 and TGF-β3 associated with the polymer targeting probe, wherein the one or more TGF active agents are released to trigger higher chondrogenic differentiation; and a third detectable tag in contact with the crosslinking agent, first biocompatible polymer, the ligand or a combination thereof, wherein the probe triggers stem cell recruitment, differentiation, and cartilage regeneration.

* * * * *